US010925772B2

(12) United States Patent
Saylor

(10) Patent No.: US 10,925,772 B2
(45) Date of Patent: Feb. 23, 2021

(54) REGENERATABLE ANTI-FOGGING ELEMENT FOR GOGGLE

(71) Applicant: Oakley, Inc., Foothill Ranch, CA (US)

(72) Inventor: Ryan Saylor, Mission Viejo, CA (US)

(73) Assignee: Oakley, Inc., Foothill Ranch (CA)

( * ) Notice: Subject to any disclaimer, the term of this patent is extended or adjusted under 35 U.S.C. 154(b) by 712 days.

(21) Appl. No.: 14/845,122

(22) Filed: Sep. 3, 2015

(65) Prior Publication Data

US 2015/0374550 A1 Dec. 31, 2015

Related U.S. Application Data

(63) Continuation of application No. PCT/US2014/020538, filed on Mar. 5, 2014.

(60) Provisional application No. 61/774,307, filed on Mar. 7, 2013.

(51) Int. Cl.
*A61F 9/02* (2006.01)

(52) U.S. Cl.
CPC .................................... *A61F 9/028* (2013.01)

(58) Field of Classification Search
CPC ... A42B 3/24; G02C 11/08; A61F 9/02; A61F 9/028; A61F 9/029
USPC .............................................................. 2/435
See application file for complete search history.

(56) References Cited

U.S. PATENT DOCUMENTS 245,268 A 8/1881 Andross
916,109 A 3/1909 Cook
1,206,457 A 11/1916 Mills
1,308,477 A 7/1919 Blanchard
1,839,386 A 1/1932 Fischer
1,918,954 A 7/1933 Baker
1,942,393 A 1/1934 Baker
1,943,910 A 1/1934 Baker
2,274,791 A 3/1942 Huggins
2,288,423 A 6/1942 Root
2,443,422 A 6/1948 Hansen
2,444,498 A 7/1948 Cochran
2,652,746 A 12/1950 Shanks
2,556,847 A 6/1951 MacLean
2,610,323 A 9/1952 Johnson
(Continued)

FOREIGN PATENT DOCUMENTS

CA 2750268 5/2015
CN 102333507 A 1/2012
(Continued)

OTHER PUBLICATIONS

"High Impact—The New Ceramic Lens", advertisement.
(Continued)

*Primary Examiner* — Sally Haden
(74) *Attorney, Agent, or Firm* — Sterne, Kessler, Goldstein & Fox P.L.L.C.

(57) ABSTRACT

A passive anti-fogging ski goggle is disclosed. In some embodiments, the goggle includes a moisture absorbing element or material, thereby reducing the amount of moisture within the space between the goggle and the wearer. In certain embodiments, the goggle includes one or more cartridges, which can be received in vents of the goggle and can include the moisture absorbing element or material. The elements can surrender moisture to the atmosphere under conditions within the normal range encountered on a ski slope.

12 Claims, 7 Drawing Sheets

(56) References Cited

U.S. PATENT DOCUMENTS 2,612,639 A 10/1952 Christensen et al.
2,615,162 A 10/1952 Christensen et al.
2,617,099 A 11/1952 Christensen et al.
2,618,782 A 11/1952 Christensen et al.
2,619,643 A 12/1952 Christensen et al.
2,619,644 A 12/1952 Christensen et al.
2,799,862 A 7/1957 Rowe
3,016,797 A 1/1962 Liautaud
3,024,341 A 3/1962 Ogle, Jr. et al.
3,160,735 A 12/1964 Aufricht
3,214,767 A 11/1965 Weber
3,229,303 A 1/1966 Jonassen
3,233,249 A 2/1966 Baratelli et al.
3,377,626 A 4/1968 Smith
3,383,707 A 5/1968 McNeill
3,395,406 A 8/1968 Smith
3,395,964 A 8/1968 Chartrice
3,552,840 A 1/1971 Braget
3,553,432 A 1/1971 Livingston et al.
3,591,864 A 7/1971 Allsop
3,691,565 A 9/1972 Galonek
3,718,937 A 3/1973 Smith
3,826,564 A 7/1974 Werling, Sr.
3,829,201 A 8/1974 Whiting
3,901,589 A 8/1975 Bienenfeld
3,931,646 A 1/1976 Loughner
3,945,044 A 3/1976 McGee et al.
4,023,214 A 5/1977 Waldherr
4,056,853 A 11/1977 Bottazzini et al.
4,076,373 A 2/1978 Moretti
4,127,682 A 11/1978 Laurin
4,138,746 A 2/1979 Bergmann
4,176,921 A 12/1979 Matthias
4,240,718 A 12/1980 Wichers
4,264,987 A 5/1981 Runckel
4,290,673 A 9/1981 Yamamoto
4,304,469 A 12/1981 Solomon
4,314,814 A 2/1982 Deroode
4,317,240 A 3/1982 Angermann et al.
4,340,282 A 7/1982 Murakami
4,357,080 A 11/1982 Solomon
4,443,893 A 4/1984 Yamamoto
4,455,689 A 6/1984 Boyer
4,471,496 A 9/1984 Gardner, Jr. et al.
4,515,448 A 5/1985 Tackles
4,527,291 A 7/1985 Nussbickl
4,563,065 A 1/1986 Kreissl
4,571,748 A 2/1986 Carroll et al.
4,584,721 A 4/1986 Yamamoto
4,616,367 A 10/1986 Jean et al.
4,633,532 A 1/1987 Yagasaki
4,638,728 A 1/1987 Elenewski
4,662,966 A 5/1987 Sumi et al.
4,670,084 A 6/1987 Durand
4,674,851 A 6/1987 Jannard
4,682,007 A 7/1987 Hollander
4,686,712 A 8/1987 Spiva
4,689,838 A 9/1987 Angermann et al.
4,707,863 A * 11/1987 McNeal .................. A61F 9/028 2/436
4,715,702 A 12/1987 Dillon
4,716,601 A 1/1988 McNeal
4,730,915 A 3/1988 Jannard
4,759,622 A 7/1988 Schmidthaler
4,813,775 A 3/1989 Kaksonen
4,822,158 A 4/1989 Porsche
4,843,655 A 7/1989 Hegendorfer
4,859,048 A 8/1989 Jannard
4,867,550 A 9/1989 Jannard
4,868,929 A 9/1989 Curcio
4,878,749 A 11/1989 McGee
4,901,374 A 2/1990 Van der Woude
4,951,322 A 8/1990 Lin
4,983,030 A 1/1991 Chandler
4,996,981 A 3/1991 Elenewski et al.
5,007,727 A 4/1991 Kahaney et al.
5,016,293 A 5/1991 Lickle
5,018,223 A 5/1991 Dawson et al.
5,048,944 A 9/1991 Porsche
5,056,163 A 10/1991 Chou
5,069,541 A 12/1991 Holmes et al.
5,144,344 A 9/1992 Takahashi et al.
5,170,502 A 12/1992 Hegendorfer et al.
5,182,586 A 1/1993 Bennato
5,182,587 A 1/1993 Hyoi
5,191,364 A 3/1993 Kopfer
5,208,614 A 5/1993 Jannard
5,220,689 A 6/1993 Miller
5,245,709 A 9/1993 Shipcott
5,257,050 A 10/1993 Wiedner
5,270,743 A 12/1993 Hofmair et al.
5,308,426 A 5/1994 Claveau
5,319,397 A 6/1994 Ryden
5,351,339 A 10/1994 Reuber et al.
5,354,966 A 10/1994 Sperbeck
5,357,292 A 10/1994 Wiedner
5,369,415 A 11/1994 Richard et al.
5,373,331 A 12/1994 Vallalla et al.
5,379,463 A 1/1995 Schleger et al.
5,390,369 A 2/1995 Tubin
5,400,089 A 3/1995 Danloup et al.
5,410,763 A 5/1995 Bolle
5,412,438 A 5/1995 Bolle
5,418,580 A 5/1995 Sondrol
5,423,092 A 6/1995 Kawai
5,428,407 A 6/1995 Sheffield
5,455,639 A 10/1995 Magdelaine et al.
5,467,148 A 11/1995 Conway
5,471,036 A 11/1995 Sperbeck
5,493,348 A 2/1996 Harald, Jr. et al.
5,517,700 A * 5/1996 Hoffman ................. A61F 9/028 2/428
5,536,828 A 7/1996 Deluca et al.
5,541,674 A 7/1996 Jannard
5,576,775 A 11/1996 Bolle
5,583,583 A 12/1996 Wilson
5,587,747 A 12/1996 Bernheiser
5,592,698 A 1/1997 Woods
5,596,339 A 1/1997 Furness, III et al.
5,602,603 A 2/1997 Bondet
5,608,470 A 3/1997 Sheffield
5,610,668 A 3/1997 Mage
5,617,588 A 4/1997 Canavan et al.
5,638,145 A 6/1997 Jannard et al.
5,641,372 A 6/1997 Okuno
5,642,530 A 7/1997 Parks
5,648,832 A 7/1997 Houston et al.
5,652,954 A 8/1997 Paiement et al.
5,657,106 A 8/1997 Herald, Jr. et al.
5,685,022 A 11/1997 Essman et al.
5,689,323 A 11/1997 Houston et al.
5,689,834 A 11/1997 Wilson
5,694,650 A 12/1997 Hong
5,708,489 A 1/1998 Jannard
5,727,251 A 3/1998 Sherlock et al.
5,752,280 A 5/1998 Hill
5,760,866 A 6/1998 Wedeck et al.
5,765,223 A 6/1998 McCausland
5,765,235 A 6/1998 Arnold
5,768,716 A 6/1998 Porsche
5,790,230 A 8/1998 Sved
5,793,463 A 8/1998 Hirschman et al.
5,796,461 A 8/1998 Stepan
5,798,017 A 8/1998 Claveau
5,802,622 A 9/1998 Baharad et al.
5,805,261 A 9/1998 Houston et al.
5,806,102 A * 9/1998 Park ......................... A42B 3/24 2/424
5,809,580 A 9/1998 Arnette
5,815,235 A 9/1998 Runckel
5,841,506 A 11/1998 Karasawa et al.
5,845,342 A * 12/1998 Park ......................... A42B 3/24 2/424
5,862,529 A 1/1999 Moodie et al.

(56) References Cited

U.S. PATENT DOCUMENTS

D405,102 S 2/1999 Moritz et al.
5,898,468 A 4/1999 Mage
5,898,469 A 4/1999 Wang
5,914,767 A 6/1999 Wedeck et al.
5,929,963 A 7/1999 McNeal
5,963,293 A 10/1999 Jannard
5,969,789 A 10/1999 Houston et al.
5,971,536 A 10/1999 Chiu
6,006,366 A 12/1999 Vondrak
6,009,564 A * 1/2000 Tackles .................... A61F 9/02 2/436
6,010,217 A 1/2000 Houston et al.
6,010,218 A 1/2000 Houston et al.
6,047,410 A 4/2000 Dondero
6,049,917 A 4/2000 Ryden
6,056,399 A 5/2000 Jannard et al.
6,062,688 A 5/2000 Vinas
D428,039 S 7/2000 Thixton
D428,620 S 7/2000 Maturaporn
6,086,199 A 7/2000 Holland et al.
6,094,751 A 8/2000 Parks
6,098,204 A 8/2000 Arnette
6,102,033 A 8/2000 Baribeau
6,105,177 A 8/2000 Paulson et al.
6,106,116 A 8/2000 Houston et al.
6,119,279 A 9/2000 Haslbeck
6,131,246 A 10/2000 Paulson et al.
6,168,271 B1 1/2001 Houston et al.
6,193,367 B1 2/2001 Lee
6,206,519 B1 3/2001 Lin
6,233,342 B1 3/2001 Fernandez
6,224,209 B1 5/2001 Chen
6,231,179 B1 5/2001 Lee
6,239,778 B1 5/2001 Palffy-Muhoray et al.
6,244,705 B1 6/2001 Ledbetter et al.
6,250,756 B1 6/2001 Jannard
6,260,964 B1 7/2001 Kroman
6,273,564 B1 8/2001 Wedeck et al.
6,276,794 B1 8/2001 Chiang
6,282,727 B1 9/2001 Lindahl
6,290,354 B1 9/2001 Safran
6,296,357 B1 10/2001 Bof
6,324,702 B1 12/2001 Spindelbalker
6,349,422 B1 2/2002 Schleger et al.
6,357,873 B1 3/2002 Spindelbalker
6,375,321 B1 4/2002 Lee et al.
6,386,703 B1 5/2002 Huang
6,405,373 B1 6/2002 Grau
6,415,452 B1 7/2002 Watanabe
6,427,254 B1 8/2002 Gardner
6,428,165 B1 8/2002 Rivera
6,464,353 B1 10/2002 Spindelbalker
6,474,812 B1 11/2002 Moon
6,477,717 B1 11/2002 Winefordner et al.
6,502,937 B2 1/2003 Yang
6,533,412 B1 3/2003 Wang et al.
6,550,912 B2 4/2003 Vitaloni
6,550,914 B1 4/2003 Kopfer
6,561,647 B1 5/2003 Chen
6,564,804 B2 5/2003 Salatka et al.
6,611,966 B1 9/2003 Yamamoto et al.
6,637,877 B1 10/2003 Hartley et al.
6,641,263 B2 11/2003 Olney
6,701,537 B1 3/2004 Stamp
6,702,439 B1 3/2004 Lee
6,712,465 B1 3/2004 Teng
6,715,157 B2 4/2004 Mage
6,718,561 B2 4/2004 Dondero
6,732,383 B2 5/2004 Cleary et al.
6,742,890 B1 6/2004 Teng
6,742,891 B2 6/2004 Chen
6,749,299 B1 6/2004 Hsu
6,772,448 B1 * 8/2004 Hockaday ............... A61F 9/028 2/435
6,783,235 B1 8/2004 Lin
6,786,592 B2 9/2004 Rivera
6,789,273 B2 9/2004 Markovitz
6,793,336 B2 9/2004 Min
6,804,835 B2 10/2004 Chou
6,817,709 B2 11/2004 Min
6,834,509 B2 12/2004 Palfy et al.
6,834,951 B2 12/2004 Xie
6,847,492 B2 1/2005 Wilson et al.
6,863,394 B1 3/2005 Nelson et al.
6,863,395 B1 3/2005 Teng
6,870,686 B2 3/2005 Wilson et al.
6,877,169 B2 4/2005 Acquaviva
D505,150 S 5/2005 Yee et al.
6,886,351 B2 5/2005 Palfy et al.
6,922,850 B1 8/2005 Arnold
6,923,537 B2 8/2005 Hartley et al.
6,926,403 B2 8/2005 Yi et al.
6,926,404 B2 8/2005 Bassahon et al.
6,928,663 B1 8/2005 Tappeiner
6,929,364 B1 8/2005 Jannard
6,938,277 B2 9/2005 Lindahl
6,948,813 B2 9/2005 Parks
6,953,247 B1 10/2005 Duffy et al.
6,959,988 B1 11/2005 Sheldon
6,964,067 B1 11/2005 Hartman
6,964,477 B1 11/2005 Teng
6,969,170 B1 11/2005 Smith
6,969,171 B2 11/2005 Lane et al.
D513,761 S 1/2006 Yee et al.
6,994,433 B2 2/2006 Hockaday et al.
7,000,263 B2 2/2006 McNeal
7,003,802 B2 2/2006 Broersma
7,023,621 B2 4/2006 Dietrich
7,029,114 B2 4/2006 Smith
7,036,152 B2 5/2006 Gafforio et al.
7,036,927 B2 5/2006 Kopfer
7,039,959 B2 5/2006 Dondero
7,058,991 B2 6/2006 Hartman
7,083,276 B2 8/2006 Olney
7,090,346 B2 8/2006 Tsai
7,091,634 B2 8/2006 Yi et al.
7,100,215 B2 9/2006 Shiue
7,126,732 B2 10/2006 McNeal et al.
7,137,153 B2 11/2006 Hussey
7,137,426 B2 11/2006 Neri et al.
7,137,700 B2 11/2006 DiChiara et al.
7,150,525 B1 12/2006 Yang
7,158,096 B1 1/2007 Spitzer
7,163,289 B2 1/2007 Wedeck et al.
D537,097 S 2/2007 Freeman
D537,860 S 3/2007 Freeman
7,192,134 B2 3/2007 Teng
7,192,137 B2 3/2007 Ishibashi et al.
7,200,875 B2 4/2007 Dondero
7,204,589 B2 4/2007 Pieterman
7,210,776 B2 5/2007 Jannard et al.
7,219,992 B1 5/2007 Wu
7,219,993 B1 5/2007 Chiou
7,222,958 B1 5/2007 Chiou
7,222,959 B2 5/2007 Jannard
D544,900 S 6/2007 Li
7,234,808 B2 6/2007 Bruck
7,237,891 B2 7/2007 Min
7,241,007 B2 7/2007 Cody
7,244,022 B2 7/2007 Lee
7,249,846 B2 7/2007 Grand et al.
7,261,410 B1 8/2007 Chen
7,267,434 B2 9/2007 Lane et al.
7,267,737 B2 9/2007 Neri et al.
7,278,733 B2 10/2007 Olney
7,296,887 B1 11/2007 Hsiung
7,328,999 B2 2/2008 Zelman
7,343,631 B2 3/2008 Lin
7,364,287 B2 4/2008 Lee et al.
7,367,669 B2 5/2008 Jannard et al.
7,370,961 B2 5/2008 Lerner et al.
7,384,141 B2 6/2008 Zelman
7,390,086 B2 6/2008 Lee
7,396,124 B1 7/2008 Wang

(56) References Cited

U.S. PATENT DOCUMENTS 7,404,217 B2 7/2008 Polinelli et al.
7,407,281 B2 8/2008 Tagawa
7,425,065 B2 9/2008 Wang
7,431,453 B2 10/2008 Hogan
7,434,929 B2 10/2008 Jackson
7,441,889 B2 10/2008 Zelman
7,452,068 B2 11/2008 Collier et al.
7,452,069 B2 11/2008 Lipawsky
7,478,906 B2 1/2009 Fielding
7,481,529 B1 1/2009 Chen
7,497,569 B2 3/2009 Webb
7,520,217 B2 4/2009 Roberts et al.
7,520,604 B2 4/2009 Choi
7,520,605 B1 4/2009 Chen
7,526,813 B2 5/2009 Tominaga et al.
7,549,180 B2 6/2009 Matsumoto et al.
7,553,013 B2 6/2009 Tsai
7,563,341 B2 7/2009 Ferguson et al.
7,585,072 B1 9/2009 Wang-Lee
7,585,073 B2 9/2009 Paolino
7,594,280 B2 9/2009 Lindahl
7,604,346 B2 10/2009 Wang
7,631,968 B1 12/2009 Dobson et al.
7,639,209 B2 12/2009 Sprague et al.
7,648,233 B2 1/2010 Blanshay et al.
7,681,257 B1 3/2010 Broersma
7,686,449 B2 3/2010 Jannard et al.
D616,485 S 5/2010 Thixton
7,712,894 B2 5/2010 Tsai
7,712,896 B1 5/2010 Lee
D616,914 S 6/2010 Moritz
7,725,959 B2 6/2010 Wang-Lee
7,740,353 B2 6/2010 Jannard
7,743,432 B2 * 6/2010 Curci .................... A61F 9/028 2/435
7,744,211 B2 6/2010 Matera
D622,303 S 8/2010 Thixton
7,771,043 B2 8/2010 Welchel et al.
7,810,174 B2 10/2010 Matera
D629,035 S 12/2010 Moritz
7,850,301 B2 12/2010 DiChiara
7,856,673 B2 12/2010 Reed
7,865,977 B2 1/2011 Rayl et al.
7,887,181 B1 2/2011 Chen
7,891,025 B2 2/2011 Kobayashi et al.
7,908,679 B2 3/2011 Wang
7,954,942 B2 6/2011 Calilung et al.
7,967,435 B1 * 6/2011 Seeto .................... A61F 9/022 351/159.57
7,971,268 B2 7/2011 Reyes et al.
8,028,350 B2 10/2011 Hogen
D649,178 S 11/2011 Moritz et al.
8,083,344 B2 12/2011 Blanshay et al.
D653,697 S 2/2012 Taylor et al.
D653,698 S 2/2012 Taylor et al.
8,192,015 B2 6/2012 Taylor et al.
8,235,523 B2 8/2012 Yang
8,303,109 B2 11/2012 Matera
8,307,466 B2 11/2012 Hsu
8,316,470 B2 11/2012 McNeal et al.
8,408,695 B2 4/2013 Calilung et al.
8,414,119 B2 4/2013 Yeh
8,469,509 B2 6/2013 Yang
8,469,510 B2 6/2013 Belbey et al.
D687,480 S 8/2013 Castro
D687,881 S 8/2013 Ginther et al.
8,534,830 B2 9/2013 Taylor et al.
D691,652 S 10/2013 Castro et al.
8,566,962 B2 10/2013 Cornelius
8,661,562 B2 3/2014 Calilung et al.
8,668,330 B2 3/2014 Reyes
8,800,067 B2 8/2014 Saylor et al.
8,850,626 B2 10/2014 Reyes et al.
8,881,316 B2 11/2014 Reyes et al.
2002/0039928 A1 4/2002 Spurgeon et al.
2003/0188376 A1 10/2003 Dondero
2004/0083540 A1 5/2004 Dondero
2004/0099972 A1 5/2004 Morris et al.
2004/0117898 A1 6/2004 Penque, Jr. et al.
2004/0139532 A1 7/2004 Parks
2004/0141147 A1 7/2004 Cyr
2004/0221375 A1 11/2004 Douglas
2005/0070434 A1 3/2005 Drake
2005/0105041 A1 5/2005 Lerner et al.
2005/0132478 A1 6/2005 Canavan
2005/0160521 A1 7/2005 Hussey
2005/0219152 A1 10/2005 Budd et al.
2005/0270477 A1 12/2005 Curci et al.
2006/0010572 A1 1/2006 Douglas
2006/0048289 A1 3/2006 Shiue
2006/0119790 A1 6/2006 Tsai
2006/0179554 A1 8/2006 Barton
2006/0191062 A1 8/2006 Matera
2006/0250571 A1 11/2006 Li
2006/0256281 A1 11/2006 Li
2006/0272078 A1 12/2006 Polinelli et al.
2006/0283555 A1 12/2006 Green
2007/0024806 A1 2/2007 Blanshay et al.
2007/0033718 A1 2/2007 Lin
2007/0091253 A1 4/2007 Chao
2007/0109490 A1 5/2007 Collier et al.
2007/0121059 A1 5/2007 Chiou
2007/0153230 A1 7/2007 Musal et al.
2007/0169252 A1 * 7/2007 Rayl .................... A61F 9/025 2/435
2007/0182916 A1 8/2007 Blanshay et al.
2007/0200997 A1 8/2007 Jannard et al.
2007/0240812 A1 10/2007 Bortolato
2007/0261782 A1 11/2007 Frye et al.
2008/0036961 A1 2/2008 Zhou
2008/0055538 A1 3/2008 Kobayashi et al.
2008/0072365 A1 3/2008 Alberto
2008/0094567 A1 4/2008 Choi
2008/0137028 A1 6/2008 Webb
2008/0155736 A1 7/2008 Paulson et al.
2008/0189838 A1 8/2008 Mage
2008/0198323 A1 8/2008 Sui Yu
2008/0266515 A1 10/2008 Hou
2008/0301858 A1 12/2008 Wang-Lee
2008/0304005 A1 12/2008 DiChiara
2009/0015929 A1 1/2009 DeJong et al.
2009/0019620 A1 1/2009 Reed
2009/0025125 A1 1/2009 Jou
2009/0038057 A1 2/2009 Tews
2009/0038059 A1 2/2009 McNeal et al.
2009/0066906 A1 3/2009 Huang
2009/0077722 A1 * 3/2009 Welchel ................ G02C 11/08 2/436
2009/0079931 A1 3/2009 Yang
2009/0100577 A1 4/2009 Kobayashi et al.
2009/0122254 A1 5/2009 Van Der Heijde et al.
2009/0151037 A1 6/2009 Hsu
2009/0180195 A1 7/2009 Cakmakci et al.
2009/0217444 A1 9/2009 Pan
2009/0222979 A1 9/2009 Wang
2009/0297756 A1 * 12/2009 Dehn .................... A42B 3/28 428/68
2009/0300830 A1 12/2009 Mage
2009/0313746 A1 12/2009 Wang
2010/0028694 A1 2/2010 Zhang et al.
2010/0053591 A1 3/2010 Gibson et al.
2010/0085533 A1 4/2010 Calilung et al.
2010/0111472 A1 5/2010 DeJong
2010/0186153 A1 7/2010 Reyes et al.
2010/0231850 A1 9/2010 Hones
2011/0007262 A1 1/2011 Taylor et al.
2011/0043644 A1 2/2011 Munger et al.
2011/0126345 A1 6/2011 Matsumoto et al.
2011/0194065 A1 8/2011 Belbey et al.
2011/0225709 A1 9/2011 Saylor et al.
2011/0225710 A1 9/2011 Reyes et al.
2011/0225711 A1 9/2011 Reyes et al.
2011/0258758 A1 10/2011 Renaud-Goud et al.
2011/0258759 A1 10/2011 Renaud-Goud et al.

(56) References Cited

U.S. PATENT DOCUMENTS

2011/0258760 A1 10/2011 Renaud-Goud et al.
2011/0296574 A1 12/2011 Morency et al.
2011/0296596 A1 12/2011 Chen
2011/0299026 A1 12/2011 Calilung et al.
2012/0038879 A1 2/2012 Reyes et al.
2012/0105740 A1 5/2012 Jannard et al.
2012/0127421 A1 5/2012 Li
2012/0137398 A1* 6/2012 Arnold .................... A61F 9/025 2/10
2012/0137414 A1 6/2012 Saylor
2012/0218504 A1 8/2012 Taylor et al.
2012/0218507 A1 8/2012 Calilung et al.
2012/0255104 A1 10/2012 Didier
2012/0324638 A1 12/2012 Tobia
2013/0043233 A1 2/2013 Elser et al.
2013/0083285 A1 4/2013 McNeal et al.
2013/0091623 A1* 4/2013 McCulloch ............. A61F 9/025 2/435
2013/0097768 A1 4/2013 Lee
2013/0104298 A1 5/2013 Domenico
2013/0104300 A1 5/2013 Park
2013/0141693 A1 6/2013 McCabe et al.
2013/0271723 A1 10/2013 Calilung et al.
2013/0286345 A1 10/2013 Belbey et al.
2014/0027436 A1 1/2014 Cornelius
2014/0033409 A1 2/2014 O'Malley et al.
2014/0059747 A1 3/2014 Belbey et al.
2014/0063438 A1 3/2014 Cater et al.
2014/0078460 A1 3/2014 Chang et al.
2014/0157496 A1 6/2014 Ginther et al.
2014/0237709 A1 8/2014 McCulloch et al.
2014/0317836 A1 10/2014 McCulloch et al.
2016/0054582 A1* 2/2016 Rauter ...................... A61F 9/02 351/155
2017/0150768 A1* 6/2017 Lipkens ................. A42B 3/226
2018/0339197 A1* 11/2018 Chiang ................ A63B 33/002

FOREIGN PATENT DOCUMENTS

EP 0121018 10/1984
EP 0496292 1/1991
EP 1810648 7/2007
EP 1830221 9/2007
FR 1126329 11/1956
FR 2088866 1/1972
FR 2626683 8/1989
FR 2688322 12/1992
FR 2684292 6/1993
FR 2800173 4/2001
FR 2812729 2/2002
GB 127410 5/1919
GB 129048 7/1919
GB 512419 9/1939
GB 2199155 6/1988
GB 2278459 11/1994
JP 59-79827 5/1984
JP 59-104127 6/1984
JP 219021 2/1990
JP H06-9636 3/1994
JP 2002-228986 8/2002
WO WO 97/21136 A1 6/1997
WO WO 97/41815 A1 11/1997
WO WO 98/30930 A1 7/1998
WO WO 00/38789 A1 7/2000
WO WO 03/023495 A2 3/2003
WO WO 2007/049070 A1 5/2007
WO WO 2007/057470 A1 5/2007
WO WO 2010/003143 A1 1/2010
WO WO 2010/081043 A2 7/2010
WO WO 2010/085416 A1 7/2010
WO WO 2012/074731 A1 6/2012
WO WO 2013/096449 A1 6/2013
WO WO 2014/093514 A1 6/2014

OTHER PUBLICATIONS

"Doubleflex®", advertisement.
"Singleflex®", advertisement.
"Alpina Carbon Quattroflex®", advertisement.
"Quattroflex® and Singleflex®—Alpina Carbon", advertisement.
Dragon, http://www.dragonalliance.com, Dragon MDX, unknown publication date, printed Jun. 20, 2014.
Goggles Giant, http://www.gogglesgiant.com, Smith Warp Racer Pack Goggles, unknown publication date, printed Jun. 20, 2014.
Goggle-Shop, http://www.goggle-shop.co.uk, Rip 'n' Roll Goggles, unknown publication date, printed Jun. 20, 2014.
Red Raven, http://www.redravenracing.com/, Red Raven Speedview goggles, unknown publication date, printed Jun. 20, 2014.
Scott, http://www.scott-sports.com, Scott Hustle MX Works Film System Goggle, unknown publication date, printed Jun. 20, 2014.
Scott, http://www.scott-sports.com, Scott RecoilXi Goggles, unknown publication date, printed Jun. 20, 2014.
Scott, http://www.scott-sports.com, Scott Tyrant Goggles, unknown publication date, printed Jun. 20, 2014.
Smith Optics, http://www.smithoptics.com, Intake Sweat-X model, unknown publication date, printed Jun. 20, 2014.
Smith Optics, http://www.smithoptics.com, Roll Offs, unknown publication date, printed Apr. 26, 2013.
Smith, http://www.smithoptics.com, Smith Fuel V.1 Max goggle, unknown publication date, printed Jun. 20, 2014.
Oakley Wind Jacket, released at least as early as Aug. 30, 2011, in 2 pages.
International Search Report and Written Opinion in Related PCT Application No. PCT/US2014/020538, dated Jun. 23, 2014; 7 pages.
International Prelirninary Report on Patentability in Related PCT Application No. PCT/US2014/020538, dated Sep. 8, 2015; 6 pages.

* cited by examiner

REGENERATABLE ANTI-FOGGING ELEMENT FOR GOGGLE

CROSS REFERENCE TO RELATED APPLICATIONS

All applications for which a foreign or domestic priority claim is identified in the Application Data Sheet as filed with the present application are hereby incorporated by reference herein under 37 C.F.R. § 1.57.

This application claims the benefit under at least 35 U.S.C. §§ 120 and 365(c) as a continuation of International Application No. PCT/US2014/020538, designating the United States, with an international filing date of Mar. 5, 2014, which claims the priority benefit under at least 35 U.S.C. § 119 of U.S. Patent Application No. 61/774,307, filed Mar. 7, 2013. The entirety of each of the above-identified applications is hereby incorporated by reference herein.

BACKGROUND

1. Field

The following disclosure relates generally to goggles such as winter sport goggles and more particularly, reversible moisture absorption systems to reduce or delay the onset of lens fogging.

2. Description of the Related Art

A wide variety of improvements have been made in recent years in the eyewear field, including eyeglasses and goggles intended for use in active sports.

Goggle applications include, for example, skiing, motocross, underwater diving masks, and a variety of industrial safety applications, such as welding and use by power equipment operators. Typically, goggles offer some degree of visibility therethrough, while also providing sealed protection to the eyes and adjacent areas of the wearer's face against particulate matter or water, without providing full head protection.

One important factor which affects vision through goggles in certain environments is fogging. Because the wearer's face is often warmer than the surrounding atmosphere for many applications (particularly for skiing, snowboarding, mountaineering, and other cold weather activities), the goggle lens is often colder than the air that is trapped between the wearer's face and the lens. Moisture in the trapped air (e.g., from the wearer's sweat) thus tends to condense upon the inside of a goggle lens. Indeed, in extremely cold conditions, as often encountered in snow-sport applications, condensed moisture can even freeze upon the lens, clouding vision considerably.

One solution to this problem in the context of winter sport goggles is to vent moisture from the wearer's side of the goggle lenses to the outside of the lens. Vents along the peripheral wall of many goggles tend not to provide a sufficient air flow to materially reduce fogging. This lack of air flow can be corrected by using larger vents, but such a design risks allowing wind, snow, hard ice particles, etc. to enter the goggles, which would be counter to the purpose for the goggles. Another known art approach has been to include forward facing vents on the lens or lower frame. However, the air exchange rate then becomes a function of forward velocity. For example, high skiing speeds may produce too much ventilation (e.g., allowing more cold air into the goggle than is needed for fogging control, which can lead to discomfort to the wearer), while slow speeds or being stationary (e.g., standing in lift lines) will result in fogging. Thus, attempts to reduce fogging by providing ventilation have been limited and substantially unsuccessful.

Another solution to the problem of fogging in goggles is to provide insulation between the lens surface closest to the wearer's face and the cold outside atmosphere. Double lens structures, having spaced inner and outer lenses, provide such insulation in many goggle designs. Illustrative prior art double lens goggles are disclosed in U.S. Pat. Nos. 3,377,626; 3,591,864; and 4,571,748. However, although double lens structures may somewhat reduce fogging, such structures may not be sufficient.

Accordingly, there remains a need for a goggle which can protect a wearer's eyes from harmful light, wind, and particles, yet simultaneously minimize fogging.

SUMMARY

In various aspects, the present disclosure relates to goggles with a single or double lens. Certain embodiments include a passive anti-fogging venting system, which is particularly useful for skiing or other winter sport or cold environment applications. Further, some of the embodiments include moisture-absorbing materials which can reduce the amount of moisture in the goggle space, and thus reduce the likelihood of or delay the onset of fogging. Moreover, in certain implementations, the moisture absorbing materials are located in removable and replaceable cartridges.

According to some embodiments, a goggle includes a goggle frame configured to be worn on a wearer's face, and a lens coupled with the frame. The goggle can also include an air flow path having at least one influent port and at least one effluent port, the path being defined at least by the frame, the lens, and the wearer's face. Further, the goggle can have an antifogging element in communication with the flow path. The antifogging element can include a hydrophilic material configured to absorb atmospheric moisture.

Various embodiments of the goggle include any one of, or any combination of, the following. In certain implementations, the goggle can also include at least one antifogging cartridge configured to be removably received in communication with the air volume entrapped between the lens and the wearer's face. The cartridge may include the antifogging element. In some embodiments of the goggle, the antifogging element is located at the influent port. In some implementations, the influent port is located on a peripheral edge such as at a bottom surface of the frame. In other implementations, the influent port is located at a top surface or a lateral surface of the frame. In certain variants, the antifogging element may comprise a hydrophilic material such as acetate. In certain instances, the hydrophilic material comprises cellulose acetate proprionate, treated to retain water.

In certain embodiments, a passive anti-fogging goggle has a goggle frame having an upper surface, a lower surface, and left and right lateral sides. The goggle can further have at least one lens held by the frame in an as-worn position, and at least a first and a second vent.

Certain embodiments of the goggle include any one of, or any combination of, the following. Some embodiments of the goggle have a cartridge configured to be received in and removable from the first and/or second vents. The cartridge can include the antifogging element. In certain variants, at least one of the antifogging elements comprises a substantially honeycomb configuration having a plurality of air flow passageways therethrough. In some implementations, the lens includes a unitary viewing window. In other implementations, the lens is divided into discrete viewing windows.

Some embodiments of the goggle include any one of, or any combination of, the following. In certain embodiments, the lens has an outer (anterior) side and an inner (posterior) side, and the total surface area of the antifogging element(s) is at least equal to the surface area of the inner side of the lens. In some instances, the surface area of the antifogging elements is at least about twice the surface area of the inner side of the lens. In some instances, the surface area of the antifogging elements is at least about five times the surface area of the inner side of the lens.

According to some embodiments, a ski goggle includes a substantially enclosed goggle space that has a volume and is defined at least by a lens, a frame, and a face of a wearer. The goggle can also include an inlet vent and an outlet vent. Further, the vents can be disposed and configured to produce a uni-directional, buoyancy-driven air flow through the goggle space. Some embodiments also include a first moisture-absorbing cartridge and a second moisture-absorbing cartridge. The first and second cartridges can be configured to be received in the inlet vent one at a time. The first and second cartridges can have the same or different levels of moisture absorbency. The goggle can be configured to allow the wearer to select, based on the desired level of moisture absorbency, which of the cartridges to install in the inlet vent.

In certain embodiments, the goggle includes any one of, or any combination of, the following. In certain implementations, at least one of the cartridges has a plurality of air flow passageways separated by a membrane which may have a substantially honeycomb configuration. At least a portion of the surface area of the honeycomb comprises a material that has been activated to enhance its moisture absorbing capacity.

In some implementations, a passive anti-fogging goggle includes a goggle frame having a top, a bottom, and sides, and a lens held by the frame in an as-worn position. The goggle can also include a heat conductive inlet vent disposed on a lower surface of the goggle. The inlet vent can be configured to receive a removable cartridge. The goggle can have an outlet vent disposed on an upper surface of the goggle. A vent shield can be mounted to the goggle frame and movable between a first position and a second position. When in the first position, the vent shield can be disposed relative to the inlet vent to inhibit undesirable elements from entering the inlet vent. When in the second position, the vent shield can be disposed so as to allow insertion and removal of the cartridge. In some embodiments, the vent shield interferes with insertion and removal of the cartridge when in the first position.

Various embodiments of the goggle include any one of, or any combination of, the following features. Certain implementations of the goggle include an antifogging element having substantially honeycomb shaped elements. In some such cases, the honeycomb shape has cells with a maximum cell width between about 1 mm and about 7 mm. The cells may have a hexagonal, triangular, circular trapezoidal or other cross sectional shape. In some variants of the goggle, the cells have a length (measured along the air flow path) of between about 0.5 cm and about 2 cm.

The aforementioned and other embodiments will become readily apparent to those skilled in the art from the following detailed description having reference to the attached figures, the disclosure not being limited to any particular embodiment disclosed. Any of the any structures, materials, steps, or other features disclosed above, or disclosed elsewhere herein, can be used in any of the embodiments within the scope of this disclosure. Any of the structures, materials, steps, or other features that are shown and/or described herein can be used in combination with any other of the structures, materials, steps, or other features that shown and/or described herein.

BRIEF DESCRIPTION OF DRAWINGS

Various embodiments are depicted in the accompanying drawings for illustrative purposes, and should in no way be interpreted as limiting the scope of the embodiments. In addition, various features of different disclosed embodiments can be combined to form additional embodiments, which are part of this disclosure.

FIG. 3*b* illustrates a repeating triangular vent shape useful in another embodiment of a goggle in accordance with certain features and advantages disclosed herein.

FIG. 3*c* illustrates a repeating rectangular vent shape useful in another embodiment of a goggle in accordance with certain features and advantages disclosed herein.

FIG. 3*d* is an octagonal vent shape useful in another embodiment of a goggle in accordance with certain features and advantages disclosed herein.

FIG. 3*e* illustrates a repeating circle vent shape useful in another embodiment of a goggle in accordance with certain features and advantages disclosed herein.

DETAILED DESCRIPTION

Figure 1:
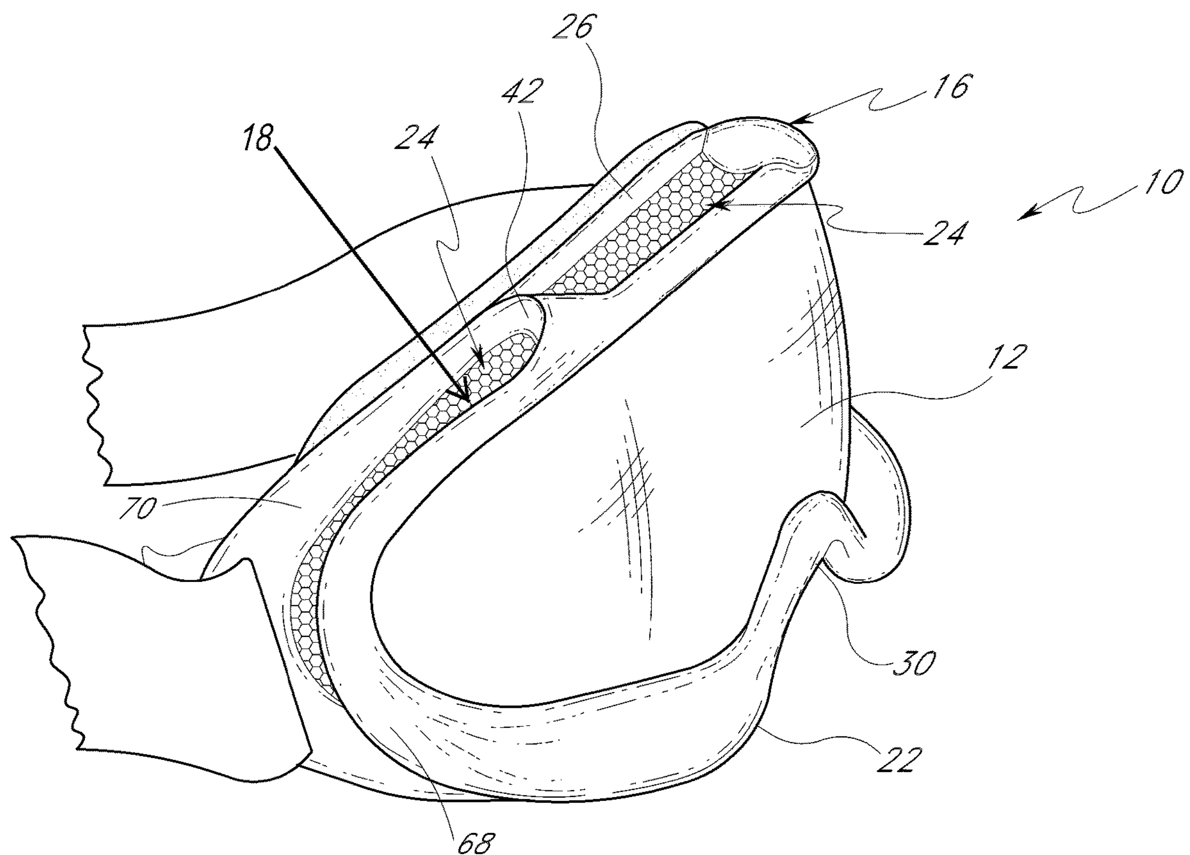
FIG. 1 illustrates a perspective view of an embodiment of a goggle in accordance with certain features and advantages disclosed herein.

Numerous embodiments of goggles that reduce, minimize, or eliminate certain of the above-noted problems are disclosed herein. These embodiments are illustrative only and are not intended in any way to restrict the scope of this disclosure and the various aspects and features presented herein. For example, although certain embodiments will be discussed below in terms of single and double lens goggles particularly adapted for snow skiing applications, the features and advantages described herein are also applicable to other goggle applications, such as other active sports (e.g., snowboarding, racquetball, basketball, racing, motocross), military, aviation, industrial, construction, laboratory and research, and otherwise. Accordingly, while certain embodiments have particular lens surface geometries, front elevational shapes, and orientations advantageous to the skiing application, the skilled artisan will readily find application for the principles disclosed herein to goggles and lenses having different geometries and orientations in the as-worn position beyond those illustrated herein. The phraseology and terminology used herein is for the purpose of description and should not be regarded as limiting. No feature, structure, or step disclosed herein is essential or indispensible.

Fogging in goggles (e.g., goggles used in winter sports) generally occurs on the cool inner lens surface due to the increased moisture content of the warm air trapped between the wearer's face and the goggle. Indeed, the air within a space between the goggle and the wearer's face can be particularly moist because of its increased temperature and the excess moisture produced by the perspiration of the wearer. A significant aspect of the behavior of moist air is that partial condensation of the water vapor in the moist air can occur when the temperature is reduced. This type of phenomenon is commonly encountered in the condensation of vapor on the inner surface of a goggle lens. For a given partial pressure of water vapor in the air, the temperature at which the vapor will condense is known as the "dew point."

The amount of moisture within a particular amount of air can be represented in a number of ways. For example, the ratio of the mass of water vapor ($m_v$) to the mass of dry air ($m_a$) in a given sample is known as the "humidity ratio," which is typically represented by the character ω.

$$\omega=m_v/m_a$$

The moisture within a particular amount of air can also be represented as "relative humidity," which is typically represented by the character φ. Relative humidity is the ratio of the mole fraction of water vapor ($\gamma_v$) in a given moist air sample to the mole fraction ($\gamma_{v,\,sat}$) water in a saturated moist air sample at the same mixture temperature and pressure.

$$\varphi=\gamma_v/\gamma_{v,sat}$$

Further, because $p_v=\gamma_v$ p and $p_g=\gamma_{v,\,sat}$, p, relative humidity can also be expressed in terms of vapor pressures:

$$\varphi=p_v/p_g$$

Values for $p_v$ and $p_g$ at various temperatures can be determined from tabulated data found in most thermodynamic text books. Relative humidity is typically stated as a percentage, and is what is generally referred to as "humidity" in typical weather reports. Thus, when a sample of moist air reaches 100% relative humidity, precipitation of water generally occurs, for example in the form of rain, snow, or condensation.

Moist air can be treated as an ideal gas in the temperature and pressure range in which a typical goggle will be used. Thus, as indicated by the Ideal Gas Law:

$$PV=nRT$$

Where:

P=Absolute pressure of gas sample;

V=Volume of gas sample;

n=moles of gas;

T=Absolute temperature (K or ° R); and

R=Ideal gas constant (8.314 J/(mole K) or 1.986 BTU/(lbmol ° R).

In general, for a given set of conditions, reducing the humidity within the goggle will move the dew point in the direction of a colder temperature.

Thus, reducing the humidity in the entrapped goggle space will either prevent fogging, or shift the dew point sufficiently to meaningfully delay the onset of fogging for a given set of environmental conditions. One prior art effort to reduce entrapped humidity has been to increase the velocity of air flow such as by the provision of forward facing vents. This can effectively reduce elevated humidity in the enclosed space, but at the expense of comfort and potentially eye protection for the wearer.

Other prior art efforts have included exposing a desiccant to the interior of the goggle. Desiccants such as molecular sieves and silica gel are materials containing tiny pores that can adsorb gases and liquids. Water molecules are small enough to pass through the pores and can therefore be adsorbed by desiccants. Once water molecules diffuse into the pores, they are trapped until a desorption process is accomplished, such as heating to evaporate the water. The pores are microscopic enough that water molecules cannot diffuse out spontaneously. So the process is generally not reversible under normal use conditions, in the environment of winter sports. Once the desiccant is saturated, it must be placed in an oven or other heat source and baked to drive off trapped water and regenerate the water absorption characteristic. This is not particularly practical on the ski slope.

In accordance with the present invention, there is provided an antifogging element having an activated surface to absorb moisture from the air entrapped by the goggle. The surface can absorb moisture and also release the moisture under conditions that are both within the normal range of conditions encountered during a typical winter sport. Thus the surface is capable of dynamic saturation and water loss depending upon the surrounding environment, and is thus regeneratable under normal use conditions.

One activated surface in accordance with the present invention comprises an activated cellulose acetate. Without being bound to any particular chemical mechanism, the following may be an explanation of the dynamic saturation characteristic of the present invention.

The chemical structure of cellulose acetate propionate is:

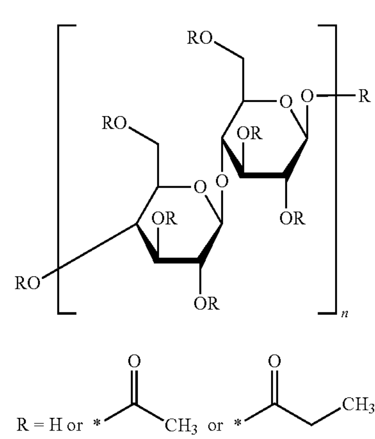

Untreated cellulose acetate propionate is hydrophobic, thus repels water. So prior art goggles that merely includes cellulose acetate propionate as a structural material would not be expected to reduce humidity within the goggle.

In accordance with some embodiments, the cellulose acetate propionate is activated, such as by being exposed to NaOH, as described in further detail below. This may convert at least some of the acetate and/or propionate moieties (═O) to hydroxyl groups (—OH). The —OH group can hydrogen bond with water (moisture) thereby at least delaying fogging on the lens. The hydrogen bonding is probably weak enough that the bonded water would come off relatively easily, under conditions normally encountered during skiing. It may also be possible that the bulk cellulose acetate propionate material is still hydrophobic, and therefore reduces the strength of the hydrogen bonding on the surface even further. So the surface can either bind or release water at either end of a normal swing in conditions under normal use.

Thus when the skier is going down the slope, the dryer air circulating into the goggle through the vent holes may shift conditions enough to break the weak hydrogen bond and cause the water to come off the treated cellulose acetate propionate, thus freeing up the —OH on the treated cellulose acetate propionate surface to bond to more water. When the skier is at the bottom of the slope waiting for the lift and the humidity and temperature rise inside the goggle, the free —OH groups are available to again hydrogen-bond with moisture and prevent a rise in humidity within the goggle thereby inhibiting fogging. In other words, when the wearer is moving relative to the environment, ambient air can circulate into the goggle, such as through the vent holes. This may change the conditions inside the space between the wearer's face and the goggle enough to break the weak hydrogen bond between the treated cellulose acetate propionate and some of the water bonded thereto. This can result in some of the water being separated from the treated cellulose acetate propionate, and can facilitate removal of that water from the space (e.g., via the airflow passing through the space). Some of the —OH groups on the treated cellulose acetate propionate surface can thus be freed, thereby rendering those —OH groups available to bond with more water. In various embodiments, such available —OH groups can counteract or reduce the rise in humidity and/or inhibit fogging on the goggle. For example, when the wearer reduces speed or stops, the airflow through the space can be reduced. This can lead to a rise in the humidity and/or temperature in the space, which can increase the likelihood of fogging. However, because the freed —OH groups are again available to hydrogen-bond with water in the space, the goggle can counteract or reduce the rise in humidity and thus inhibit fogging on the goggle.

How much water can be "captured" by the treated cellulose acetate propionate would among other things be a function of the available surface area where —OH is available to hydrogen-bond with water. Honeycomb or other multiple passageway structures increase the surface area of the cellulose acetate propionate that can be exposed to water, so these structures will optimize the regeneratable under normal use conditions characteristic of the surface.

The antifogging element of the present invention thus includes at least a surface layer of a material or a material having a surface which absorbs water. The water absorbing surface will generally be a surface of the goggle that is exposed to the entrapped air space between the lens and the wearer's face, or may be in air flow communication with that entrapped space. The surface may also be on the posterior surface of the lens. For optimum optical performance, however, it may be desirable to provide the activated surface described herein such that it is positioned outside of the primary line of sight, or such that it avoids the lens entirely. Preferably, the water may be released back into the atmosphere under conditions that do not require the use of chemicals or high temperature ovens. Preferably, the water capacity of the antifogging element can be substantially regenerated at temperatures of less than about 150° F., preferably less than 100 F.°, and in many embodiments, less than about 80° F. This may be accomplished by the use of a material which binds weakly to water, such via hydrogen bonding. Any of a variety of materials having surface hydroxyl groups may be suitable, depending upon the desired performance characteristics. Surfaces which comprise acetate and/or propionate moieties can be treated such as disclosed herein to increase the number of hydroxyl groups and create a regeneratable water absorption characteristic.

As indicated above, in certain implementations of the antifogging element, at least some moieties (═O) on the activated surface have been converted to hydroxyl groups (—OH) to produce a moisture absorbing surface or portion. Production of the moisture absorbing surface or portion can begin with providing a goggle frame, moisture absorbing element or other structure having a surface which will be in communication with the entrapped air space as the goggle is worn. The surface can be made of cellulose acetate propionate. The surface can be cleaned, such as with a reverse osmosis water bath with bubbling air for agitation and a flow of about 0.5 gallons/minute.

The surface can be bathed in a caustic medium, such as NaOH. For example, the surface can be bathed in NaOH at about 9.2%-9.4% solution in reverse osmosis water for about 15 minutes, with about a 1.5 gallon/minute flow rate, and at about room temperature. Exposure to the caustic medium can facilitate a conversion of the surface For example, when a surface made of cellulose acetate propionate is exposed to NaOH, a portion of the surface can be converted to a polysaccharide. In general, the depth and effectiveness of the surface conversion can be increased with an increase in the caustic percentage, the exposure time, or both. In some embodiments, the surface is rinsed to inhibit or terminate further conversion and/or to wash away residual caustic. For example, the surface can be rinsed with a reverse osmosis water bath for about 15 minutes with bubbling air for agitation and a flow of about 0.5 gallons/minute.

In certain implementations, the surface is bathed in an aldehyde, such as glyoxal or formaldehyde, to effectively reverse the surface conversion from polysaccharide. This can produce a sort of membrane that can facilitate vapor transfer yet be durable enough to resist scratching. In some implementations, the surface is bathed in glyoxal at 10% solution in reverse osmosis water, at a flow of about 3 gallons/minute, at about room temperature, and for a time period of about 3 minutes. The surface can be rinsed (e.g., for about 104 seconds) with reverse osmosis water to inhibit or terminate the reversing reaction and/or to wash away residual aldehyde (e.g., glyoxal). According to some implementations, the surface is then cured to evaporate any residual chemicals and/or to solidify the membrane. For example, the surface can be convectively thermally cured for about 45 minutes at about 70° C.

Referring to FIGS. 1-9, illustrative ski goggles 10 are illustrated. The goggle 10 includes an outer lens 12 held by a frame 16. Certain embodiments also include an inner (posterior) lens, which can be held by the frame 16 as well. The lens 12 includes an outer (anterior) surface 12' and an inner surface 12" (see FIG. 8). Likewise, in embodiments including the inner lens, the inner lens can have an outer surface and an inner surface. Generally, if fogging would occur, it would occur on the inner surface 12" (for embodiments with just the outer lens 12) on the inner surface of the posterior lens (for embodiments also including the inner lens). The illustrated outer lens 12 is a unitary lens, which is configured to extend across the vision of both eyes in an as-worn orientation upon a wearer's head. Other embodiments include a separate outer lens 12 for each eye.

In some embodiments, the goggle 10 has a double frame construction. For example, the goggle 10 can include an outer or front frame portion 68, bounding the lens 12 (or lenses), and an inner or rear frame portion 70 spaced behind the front frame portion 68 (see, e.g., FIGS. 1 and 8). In some such instances, the front frame portion 68 is spaced by about 1 cm to about 2 cm from the rear frame portion 70 at the top 26 and/or bottom of the goggle 10 (see, e.g., FIG. 2). The spacing typically tapers slightly down the height of the goggle 10 such that the portions 68, 70 merge at the bottom of the medial recess 30 (see, e.g., FIG. 3). As shown in FIG. 1, the frame portions 68, 70 can be connected to one another by one or two or more relatively thick bridge strut portions 42 at or near the top portion of the frame 16. As shown, in some configurations, the bridge strut portions 42 have a curved configuration with a concave side facing laterally away from the central medial portion of the frame 16.

The rear surface of the rear frame portion 70 is typically lined with a cushioning material 60. In certain embodiments, the cushioning material 60 comprises an inner layer 72, an intermediate layer 74, and an outer layer 76 (see, e.g., FIG. 8). The inner layer 72 preferably comprises a soft, matted or woven fiber to prevent chaffing the wearer's face, such as Polartec®, available from Malden Mills Industries, Lawrence, Mass. The intermediate layer 74 can include a resilient, deformable material such as an open cell polyurethane foam, while the outer layer 76 can be a relatively more dense foam material that is readily adhered to the material of the rear frame portion 70.

Figure 2:
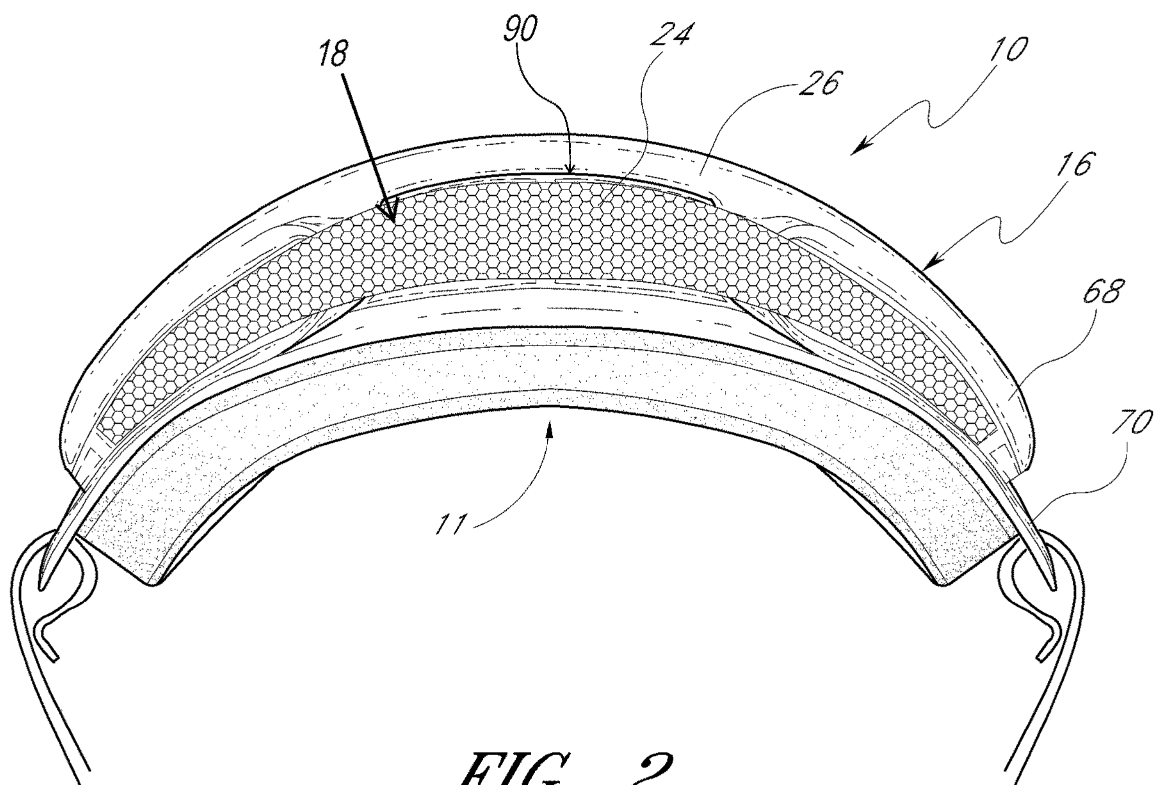
FIG. 2 illustrates a top view of another embodiment of a goggle in accordance with certain features and advantages disclosed herein.

In some implementations, the goggle 10 includes an antifogging element 18, at least one inlet vent 20 on a lower edge 22 of the frame (see, e.g., FIGS. 3 and 8), and at least one outlet vent 24 on an upper edge 26 of the frame (see, e.g., FIGS. 1 and 2). The terms "inlet" and "outlet" are used for convenience and do not necessarily imply a direction of air flow. All of the vents described herein provide communication between the entrapped space 11 between the lens and the wearer's face, and the outside environment. In some embodiments, the inlet vents 20 can each permanently or removably receive the antifogging element 18 or a cartridge containing an antifogging element. Alternately, or in addition, the outlet vents 24 can each permanently or removably receive the antifogging element 18.

In some implementations, the goggle 10 includes an antifogging element 18, at least one inlet vent 20 on a lower edge 22 of the frame (see, e.g., FIGS. 3 and 8), and at least one outlet vent 24 on the top 26 of the goggle 10 (see, e.g., FIGS. 1 and 2). The terms "inlet" and "outlet" are used for convenience and do not necessarily imply a direction of air flow. All of the vents described herein provide communication between the entrapped space 11 between the lens and the wearer's face, and the outside environment. In some embodiments, the inlet vents 20 can each permanently or removably receive the antifogging element 18 or a cartridge containing an antifogging element. Alternately, or in addition, the outlet vents 24 can each permanently or removably receive the antifogging element 18.

In some implementations, the inlet vents 20 are bilaterally symmetric mirror images of each other across the midline of the goggle. Furthermore, two or three or more inlet vents 20 can be spaced apart from each other along the frame. For example, in the embodiment shown in FIG. 3, the inlet vents 20 are spaced apart by, and do not extend through, the medial recess 30.

In certain embodiments, two inlet vents 20 are provided such that one vent is located generally below each of the wearer's eyes and the two inlet vents 20 are separated by a medial recess 30 of the goggle 10. In other embodiments, one unitary inlet vent extends substantially across the entire bottom of the goggle 10, including the medial recess 30. The outlet vent at the top of the goggle may extend at least about 50%, sometimes at least about 70% and in some embodiments at least about 85% of the width of the front frame.

In some embodiments, the inlet and/or outlet vents 20, 24 are protected and/or at least partly covered by one or more vent shields 32. See FIG. 6. The vent shields 32 can, for example, direct wind, as well as snow, debris, and other particulates away from the vents 20, 24. In certain embodiments, the vent shields 32 are configured to influence (e.g., to increase or reduce) the rate of airflow through the goggle 10. For example, the vent shields 32 can be configured to mitigate the effect of forward velocity on the rate of airflow through the goggle 10.

The inlet vents 20 can be mounted between the front and rear frame portions 68, 70 and can be configured to direct air upwardly into a goggle space 11, which can be an enclosed cavity or space defined between the lens 12 and wearer's face in the as-worn condition. As discussed in further detail below, such a configuration can cause air to flow vertically through the goggle space 11, before being exhausted through the outlet vent 24 at the top of the goggle. Alternatively, the goggle 10 may be configured to include an outer lens 12 and an inner lens 14 with vents disposed to produce a similar free convective flow through the space between the outer and inner lenses 12, 14.

In certain implementations, the goggle 10 is configured to produce a constant (e.g., substantially uninterrupted) unidirectional flow of air through the goggle space 11 by employing free convection flow. Free convection flow results when warmer, less dense air rises in a column of cooler, denser, air due to buoyant forces.

Figures 8, 8A, 8B:
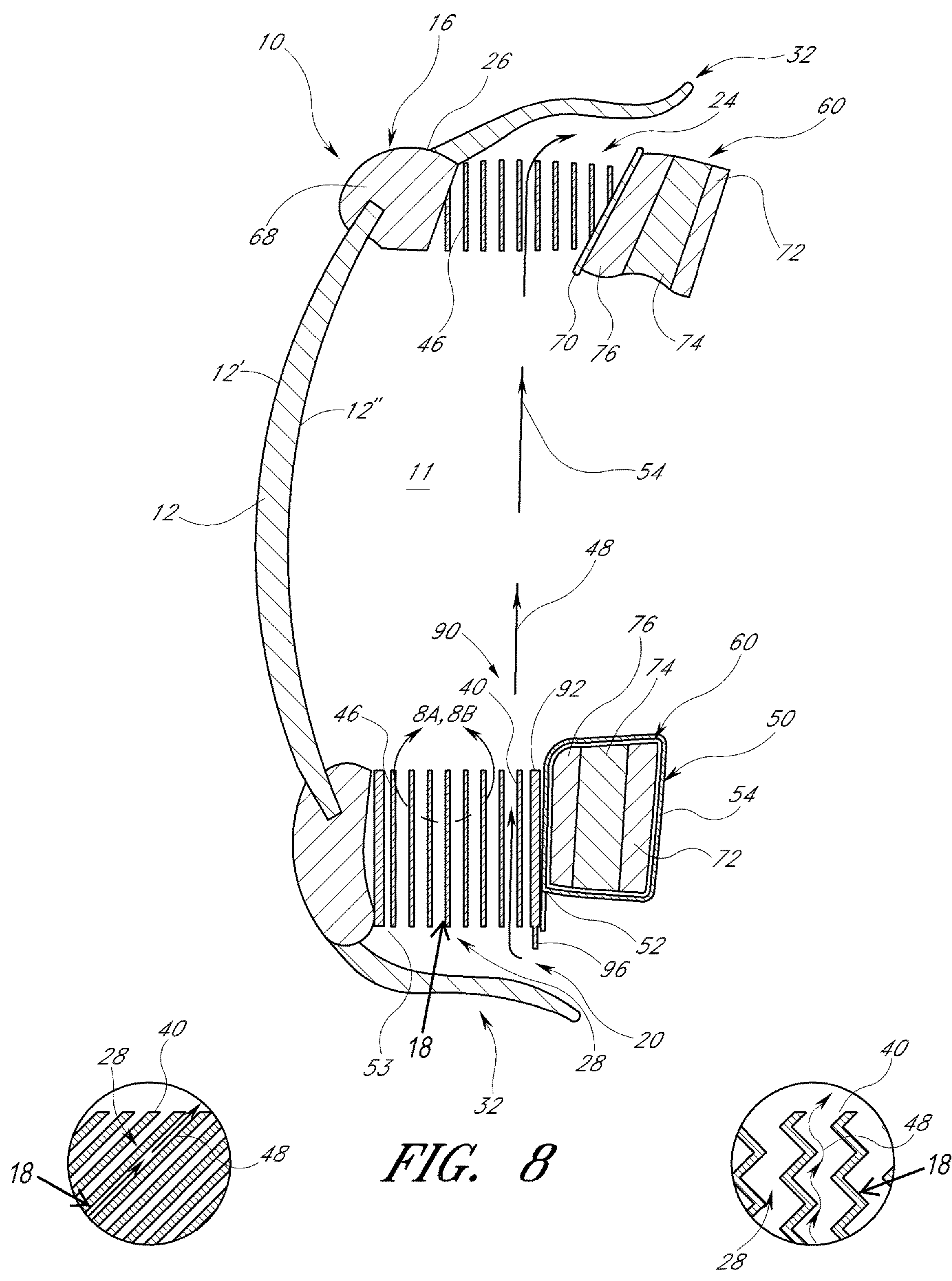
FIG. 8 illustrates a vertical cross-sectional view of the goggle of FIG. 7, taken along the line 8-8, with a vent shield in a first position and a cartridge in an installed position.
FIG. 8*a* illustrates an alternative embodiment of an inlet vent flow path configuration for an antifogging element in the goggle of FIG. 7.
FIG. 8*b* illustrates an alternative embodiment of an inlet vent flow path configuration for an antifogging element in the goggle of FIG. 7.

In order to produce the free convection flow, the goggle 10 can be configured to transfer heat to structures in communication with the air flow path which will act as the heat exchangers 28. For example, as shown in FIG. 8, one or more heat conductive strips 50 may be provided and disposed such that a first portion 52 of the strips 50 is in contact with the inlet vent 20 and/or antifogging element 18, and a second portion 54 is in thermal communication with a wearer's face. Thus, the one or more strips 50 can allow heat to be conducted from the wearer's face to the heat conductive material of the heat exchangers 28. The strips may be made of a thin, heat conductive material such as aluminum tape or other metal.

In certain embodiments, such as is illustrated in FIG. 8, the heat conductive strip 50 wraps around the cushioning material 60 of the goggle frame 16. In other embodiments, the heat conductive strip 50 extends through one or more layers of the cushioning material 60 or otherwise provides the desired heat conduction. In certain implementations, the cushioning material 60 between the heat exchangers 28 and the wearer's face may be made from, or include, a thermally conductive material (e.g., a gel) that conducts heat from the wearer's face to the heat exchangers 28. In some embodiments, heat from an auxiliary heat source (not shown), such as an electrical resistance heater or chemical heaters (e.g., a methanol fuel cell), is transmitted to the heat exchangers 28.

Figure 1A:
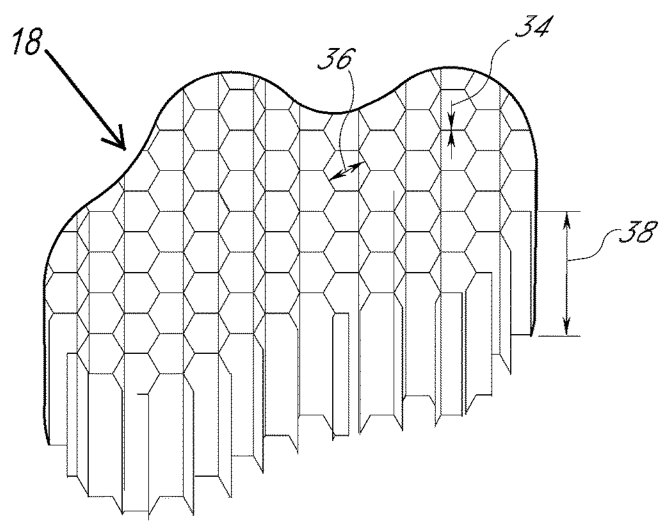
FIG. 1*a* illustrates a cutaway view of an antifogging element within a vent of the goggle of FIG. 1.

As shown in FIG. 1*a*, in certain embodiments, the anti-fogging element 18 has a honeycomb shape. Such a configuration can, for example, provide increased heat transfer in an embodiment configured for heat exchange and decreased air flow resistance. Honeycomb type configurations also can optimize the surface area exposed to air, thereby optimizing the capacity for water absorption. In such configurations, the cells of the honeycomb can include a wall thickness 34, a cell diameter 36, and a flow path length 38. For example, in some embodiments, the antifogging elements 18 include a honeycomb of about 20 to 100 hexagonal cells. In certain such embodiments, each cell has a wall thickness 34 of no more than about 0.01 inches, diameter 36 of no more than about ¼ inches, and length 38 of about 0.5 to about 1.5 inches.

In certain arrangements, a honeycomb cell for use in the antifogging element 18 has a diameter in the range of about 1 mm to about 13 mm. In other embodiments, the honeycomb cell has a diameter between about 2 mm and about 7 mm. In certain embodiments, the flow path length 38 is at least about 0.5 cm. In another embodiment, the length 38 is within the range of from about 1 cm to about 3 cm for a linear flow path. Greater lengths may be readily obtained using tortuous flow path geometries as discussed elsewhere herein.

In certain embodiments, the sum of the cross-sectional areas of the cells of the antifogging element 18 is greater than about 2 $cm^2$. In some embodiments, the sum of the cross-sectional areas of the cells is greater than about 5 $cm^2$. In certain embodiments, the sum of the cross-sectional areas of the cells is within the range of from about 5 $cm^2$ to about 30 $cm^2$.

In certain implementations, the moisture absorbing surface or portion of the antifogging element 18 includes a hydrophilic material, such as an activated acetate. For example, some embodiments comprise cellulose acetate proprionate, polycellulose acetate, cellulose acetate, cellulose acetobutyrate, cellulose acetopropionate, or otherwise. In certain implementations, the moisture absorbing portion includes a hygroscopic material. For example, some embodiments comprise nylon, acrylonitrile butadiene styrene, polycarbonate, cellulose, and polymethyl methacrylate, a salt, or otherwise. In some embodiments, the moisture absorbing portion is a capsule, bag, pellet, or otherwise that is received in the goggle 10 (e.g., in a chamber in the antifogging element 18). In other embodiments, the moisture absorbing portion is part of another component of the goggle 10, such as a module fit within a complementary structure such as an intake port and/or be part of the heat exchangers 28, and can be removable and replaceable.

The moisture absorbing portion of the antifogging element 18 can be disposed in most any location of the goggle 10, preferably other than on the lens or within the straight ahead viewing axis. For example, in some embodiments, the antifogging element 18 is positioned within or across the opening of an inlet vent 20 or outlet vent 24. In further embodiments, the moisture absorbing portion comprises fins, plates or honeycomb structure attached to the inside of the goggle 10 along the lateral sides, top and or bottom of the frame. In certain embodiments, the frame 16 includes the moisture absorbing surface or portion of the antifogging element 18. For example, a portion of the frame 16 (e.g., the portion of the frame contacts the airflow through the internal air space 11) can be made of activated acetate.

The moisture absorbing surface disclosed herein can be provided on any structure that places the surface in communication with the entrapped air space between the lens and the wearer's face. Although described primarily herein in the context of removable anti fogging elements, the surface can alternatively be permanently carried by the goggle. This may be accomplished by constructing any of the anti-fogging structures disclosed elsewhere herein, and permanently bonding them to the goggle, or forming them integrally with the goggle. Alternatively, the moisture absorbing surface can be formed directly on, or attached to any one or more of the front frame, rear frame or struts connecting the front and rear frame. The surface may be formed on or carried by the top, bottom, left or right side of the goggle, or at least two or three or all of the foregoing. Hybrid goggles may be desirable for certain applications, in which a receptacle is provided for removably receiving one or more anti-fogging elements in addition to one or more moisture absorbing surfaces which are permanently formed on or carried by any of the foregoing portions of the goggle. Manufacturing techniques will be understood by those of skill in the art in view of the disclosure herein, and may include, for example, co-molding the acetate component with a urethane frame component and subsequently treating the acetate surface as disclosed elsewhere herein.

Figure 3:
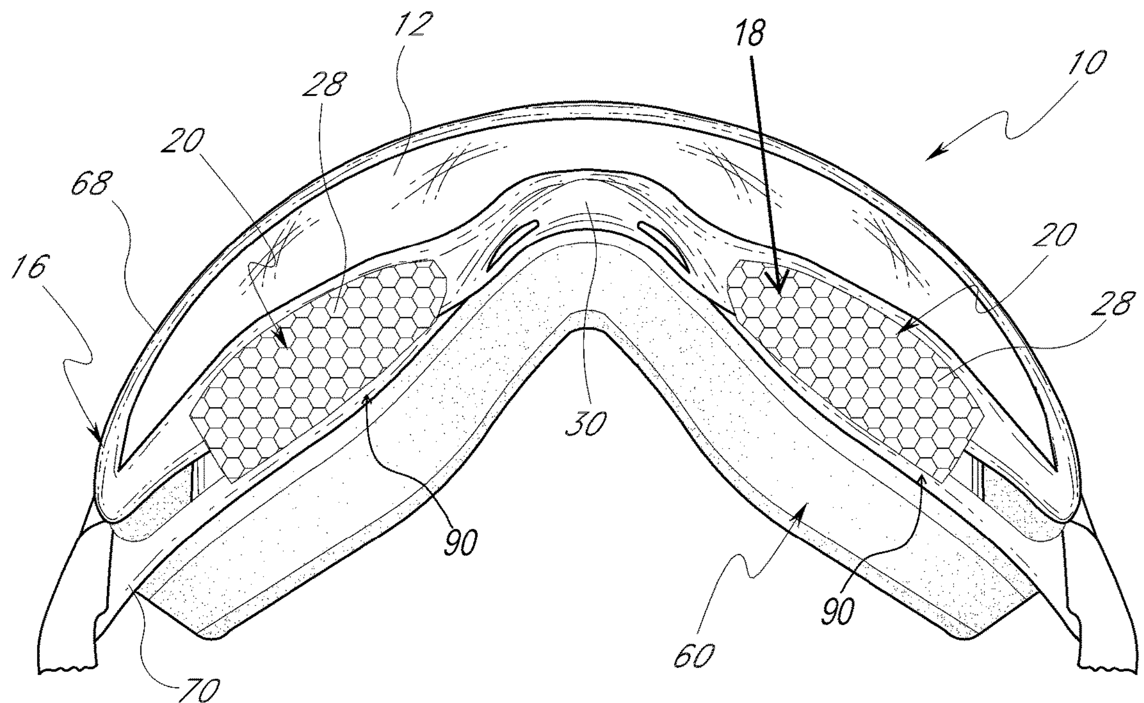
FIG. 3 illustrates a bottom view of another embodiment of a goggle in accordance with certain features and advantages disclosed herein.
Figure 3A:
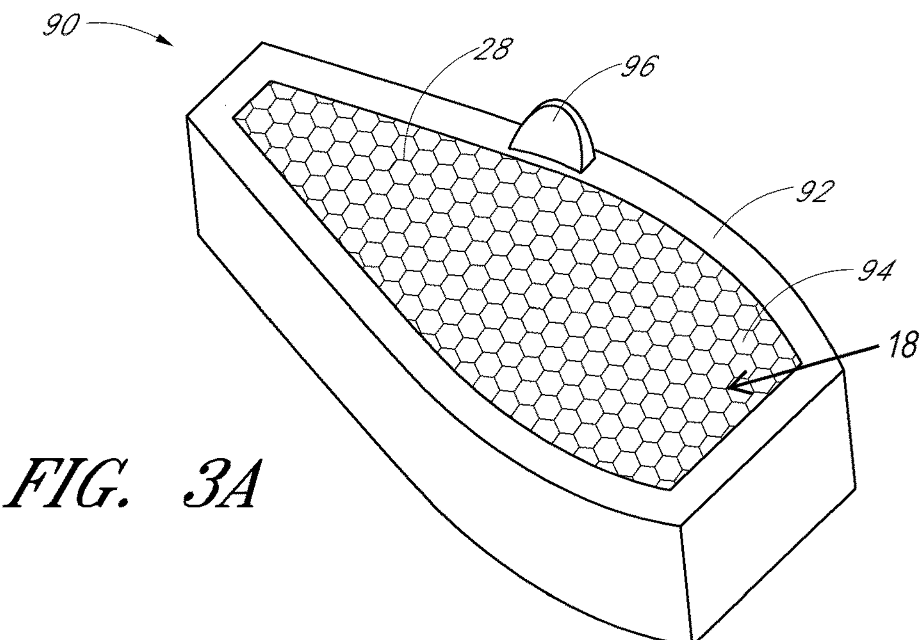
FIG. 3*a* illustrates an antifogging cartridge for positioning in a vent.
Figure 3B:
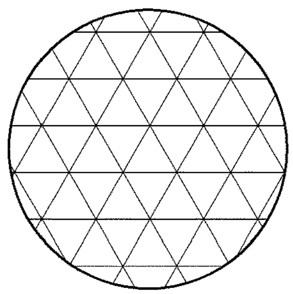
FIG. 3*b*-3*e* illustrates alternative air channel shapes useful in antifogging elements.

In certain implementations, the antifogging element 18 is provided in a cartridge 90. Generally, the cartridge 90 is configured to be received in, and removable from, a portion of the goggle 10. For example, in some embodiments, the cartridge 90 is configured to be received within a vent. In certain such instances, the cartridge 90 can have a complementary size and shape to the vent thereby allowing the cartridge 90 to be slidably received in the vent. For example, FIG. 3 schematically illustrates an embodiment of the goggle 10 where cartridge 90 is configured to be slidably received in an intake port of FIG. 3. In some embodiments, the cartridge 90 is configured to be slidably received in the outlet vent 24. As shown, the cartridge 90 can include a sidewall 92 and a cavity 94. Cavity 94 contains a honeycomb or other structure which carries the water absorbing surface, and a plurality of air passageways extending from the first side of the cartridge to a second side of the cartridge. In some embodiments, the cartridge 90 has a grip 96, which can facilitate grasping of the cartridge 90, such as during removal of the cartridge 90 from the goggle.

The goggle and/or the cartridge 90 may include complementary locking structures to maintain the cartridge 90 in the vent 20 and/or to inhibit unintentional removal of the cartridge 90. For example, the vent 20 and/or the cartridge 90 can have a latching mechanism configured to inhibit or prevent unintentional removal of the cartridge 90. In some embodiments, the vent 20 includes a detent (e.g., a spring-loaded ball or deformable metal or plastic detent) and the sidewall 92 includes a recess configured to receive the detent when the cartridge 90 is received in the vent 20. In other embodiments, the cartridge 90 has a notch that engages with a tab in the vent 20. In yet other embodiments, the cartridge 90 is maintained in the vent 20 by a friction fit. In certain variants, the cartridge 90 is secured in the goggle 10 with a threaded fastener (e.g., a set screw), hook and loop fastener, cotter pin, adhesive, or otherwise. As noted above, certain embodiments of the cartridge 90 are removable from the goggle 10, thus the locking features of such embodiments are generally configured to be disengagable (e.g., by a person wearing gloves). In other embodiments, the cartridge

90 is configured to be substantially non-removable from the goggle 10 (e.g., from the vent 20).

Embodiments of the goggle 10 with removable cartridges 90 can, for example, provide the ability to swap one cartridge 90 for another cartridge 90. For example, should a particular cartridge 90 become clogged with snow or debris, or saturated, that cartridge 90 can be replaced with a different, fresh cartridge 90 having additional water capacity.

In certain implementations, the ability to swap cartridges 90 facilitates customizing the goggle 10, for example, based on the environmental conditions. For example, the wearer could insert cartridges 90 with a relatively large cell diameter 36 (see FIG. 1*a*), thereby increasing the amount of airflow though the goggle space 11. Under different conditions, the wearer could insert cartridges 80 having a relatively small cell diameter 36, thereby limiting the amount of cold ambient air that enters the goggle space 11.

As another example, a wearer expecting a period of exertion (e.g., when climbing a portion of a mountain during backcountry skiing), which can correspond with an expected increase in perspiration, could select a cartridge 90 with a higher level of moisture absorbency for the exertion period and switch to a cartridge 90 with a lower level of moisture absorbency in other periods (e.g., during the decent of the mountain). Furthermore, the ability to swap cartridges 90 can allow replacement of a particular cartridge 90 that has become saturated, damaged, or otherwise in need of renewal.

With reference to FIG. 2, the outlet vent 24 can be sized to allow sufficient air flow out the top 26 of the goggle 10, while limiting the ingress of contaminants and other matter, such as snow, dirt, debris, etc. In certain embodiments, the outlet vent 24 is configured to block or limit the amount of light able to pass through the outlet vent 24. Typically, the flow rate of air through the outlet vent 24 is at least partly dependent on the open space in the outlet vent 24 area through which the air may flow. Thus, in some embodiments, the outlet vent 24 comprises at least as much open area as the total open area of the inlet vents 20. “Open area” refers to the total area of the inlet and outlet vents 20, 24 through which air may flow (e.g., the area represented by the “white space” between the cells of the honeycomb in FIGS. 2 and 3).

The outlet vent 24 may comprise a variety of shapes. For example, the outlet vent 24 can comprise a single large rectangular or otherwise shaped opening of sufficient area; however, this would have the disadvantage of potentially allowing substantial amounts of solid objects and/or light to enter the goggle. Thus, the outlet vent preferably comprises a plurality of smaller openings that are sized and arranged to provide a sufficient flow area and substantially limit the ability of contaminants and other matter to enter the goggle. In some embodiments, a single outlet vent 24 has a plurality of cells and extends substantially across the entire top 26 of the goggle 10. In another embodiment, the outlet vent 24 is divided into a plurality of sections (see, e.g., FIG. 1). In certain such arrangements, the sections of the outlet vent 24 are partitioned by solid separators 42, which can also provide structural support to the goggle 10.

Figure 4:
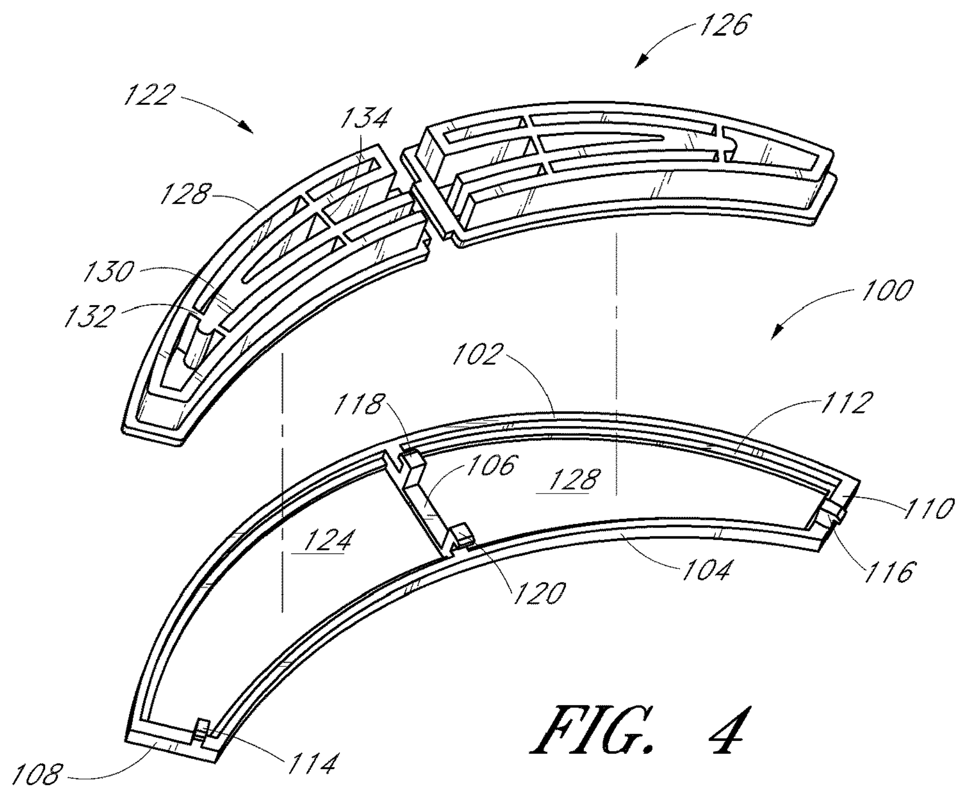
FIG. 4 illustrates a removable antifogging cartridge in accordance with certain features and advantages disclosed herein.
Figure 5:
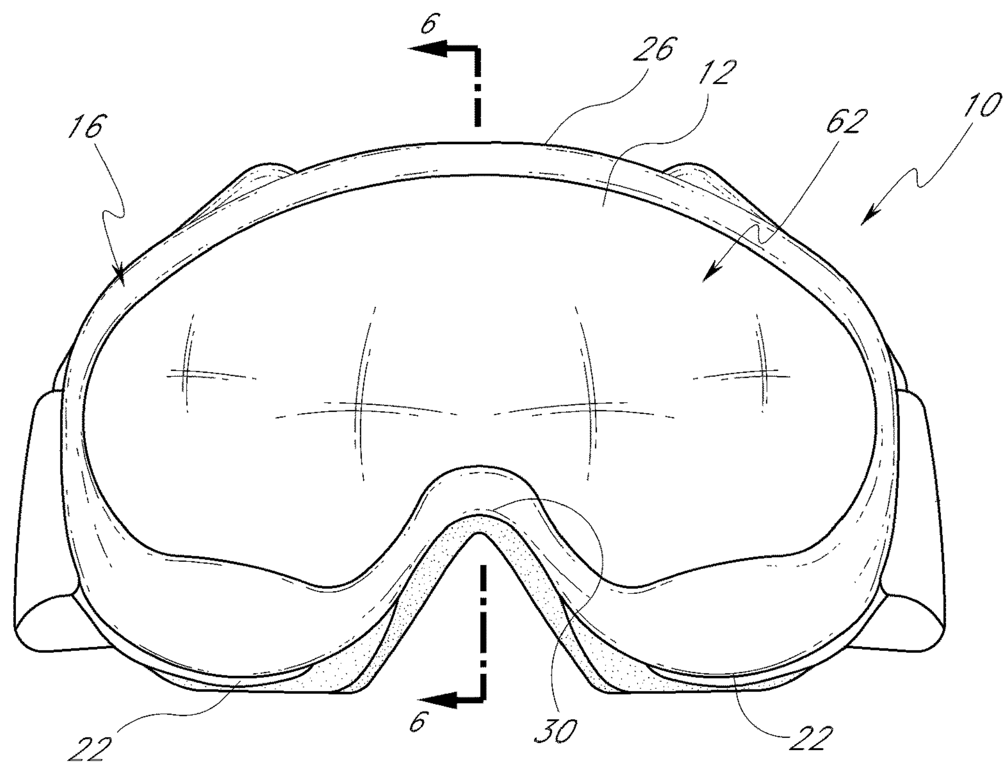
FIG. 5 illustrates a front view of a goggle.
Figure 6:
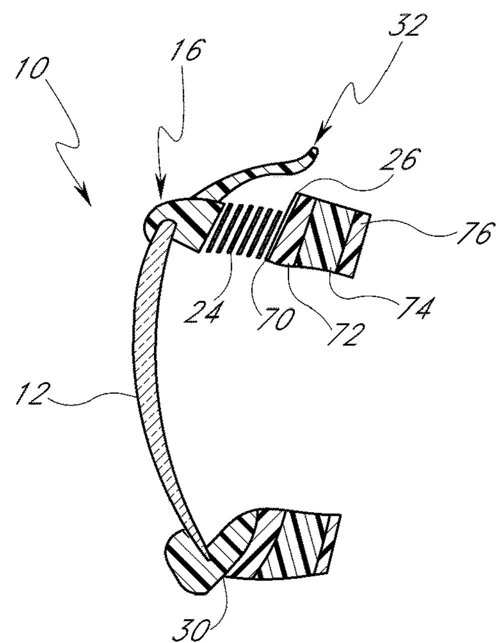
FIG. 6 illustrates a vertical cross-sectional view of FIG. 5, taken along the line 6-6.

Referring to FIG. 4, there is illustrated a further example of an antifogging element for mounting on the upper frame of a goggle. The antifogging element comprises a frame 100 which may include an anterior support 102 and a posterior support 104. At least one strut such as central strut 106 and first end strut 108 and second end strut 110 may be utilized to connect the anterior support 102 and posterior support 104 to form a carrier for retaining the water absorption cartridges. The frame 100 may include at least one retention structure having a support surface for supporting and retaining a cartridge therein. For example, the anterior support 102 and/or posterior support 104 may be provided with a flange 112 which carries a support surface to retain the cartridge. In addition, at least a first connector 114 and a second connector 116 are attached to the frame, for connecting the frame to a corresponding connector on the goggle. In the illustrated embodiment, a third connector 118 and a fourth connector 120 are provided on the central strut 106. The connector may include an interference fit surface, such as on a latch, or hook, for engaging a corresponding structure on the goggle frame.

The illustrated embodiment provides a carrier to carry two cartridges for mounting on the top of a goggle. A first cartridge 122 is receivable within a corresponding cavity 124 in the frame 100. A second cartridge 126 may be positioned in a second aperture 128 defined by the frame 100, to complete the antifogging element. Each of the first cartridge 122 and second cartridge 126 comprises a side wall 128 which defines a plurality of flow paths 130 through the cartridge. As described elsewhere herein, the side wall 128 is preferably configured to optimize (e.g. generally maximize) the surface area of the side wall 128 exposed to air passing through the flow path 130. Thus, honeycomb, zigzag or undulating structures may be utilized. In the illustrated embodiment, the sidewall 128 has at least four segments, and at least a first strut 132 and second strut 134 are provided to additionally increase the exposed surface area of the sidewall 128. Any of a variety of specific configurations can be constructed, depending upon the desired performance, and other design constraints. The first and second cartridges may be permanently mounted in the frame 100 so that the frame 100 may be connected and disconnected from the goggle as a unit. Alternatively, the frame 100 may be connected to the goggle and the first cartridge 122 and second cartridge 126 may be removably connectable to the frame 100.

Figure 7:
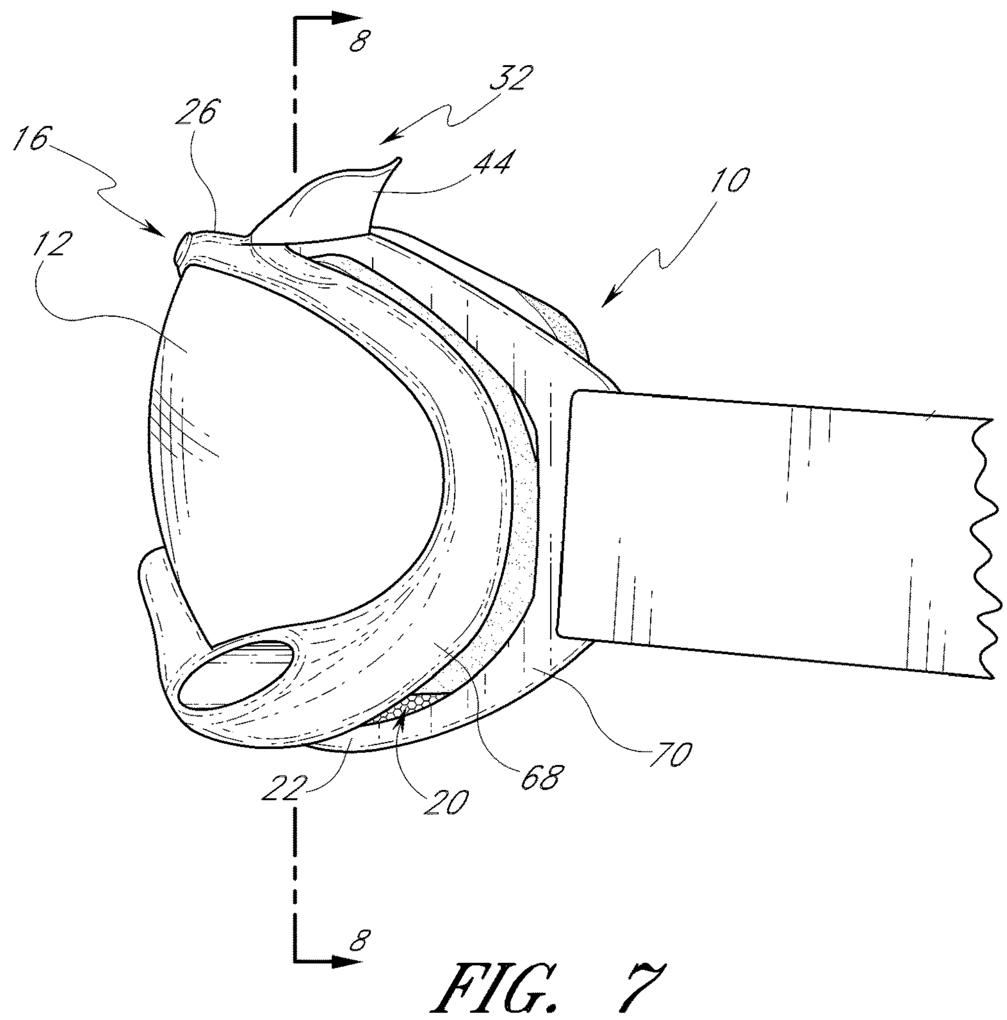
FIG. 7 illustrates a side view of another embodiment of a goggle in accordance with certain features and advantages disclosed herein.
Figure 9:
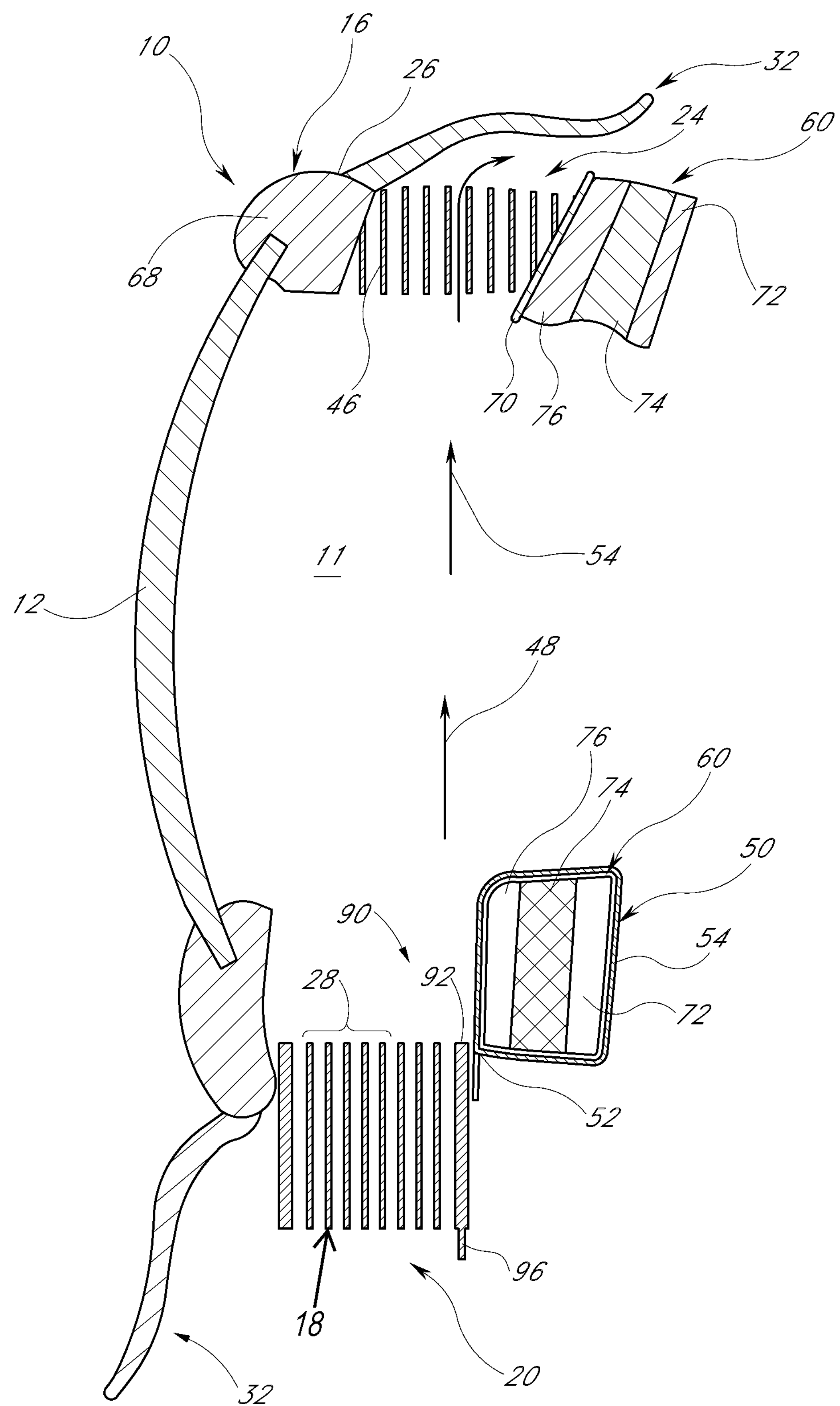
FIG. 9 illustrates the goggles of FIG. 8 with the vent shield in a second position and the cartridge in a partially installed position.

With reference to FIGS. 7-9, the desired rate of air flow through the goggle space 11 may vary depending on the amount of air that the goggle 10 entraps and the particular environmental conditions in which the goggle 10 is intended to be used. Various sizes of the goggle 10, when on a wearer’s face, entrap different amounts of air. In some embodiments, the entrapped air volume within a goggle is within the range of from about 130 $cm^3$ to about 200 $cm^3$. In general, for a given environmental condition, the greater the amount of entrapped air in the goggle space 11, the greater the desired rate of flow through the goggle space 11.

The total air flow through the goggle space 11 may be represented by an air replacement rate. The “air replacement rate” is the frequency at which the volume of entrapped air in the goggle space 11 is substantially entirely replaced. Appropriate air replacement rates for various expected use conditions can be readily determined taking into account the desired performance characteristics. For example, some embodiments of the goggle 10 having desired features and advantages adapted for use in standard snow skiing applications have a steady-state air replacement rate of at least about once per minute. Other such embodiments have a steady-state air replacement rate within the range of from about one replacement every 5 seconds to about one replacement every 2 minutes. For example, in some particularly cold or high-moisture use conditions, it may be desirable to have a replacement rate such that the entrapped air is replaced every 10 seconds. In slightly less severe conditions, an entrapped air replacement every 30 seconds may be sufficient. Thus, for example, in embodiments of the goggle 10 having an enclosed volume of about 150 $cm^3$, a desirable flow rate through the goggle may be in the range of about 75 $cm^3$/min to about 1,800 $cm^3$/min. Of course, the flow rate of air through the goggle space 11 may be optimized for various conditions and users.

The dimensions and configuration of the honeycomb or other antifogging element 18 structure is preferably chosen to maximize air flow, while reducing the likelihood of (preferably eliminating) the ability of contaminants or other matter (e.g., snow, dirt, debris, etc.) to enter the outlet vent 24 and optimize surface area when the outlet vent is intended to function as an antifogging element. Certain aspects of the ability of the honeycomb-shaped outlet vents 24 to block snow and particulate ingress can be quantified by the relationship $1/D^2$, where 1 is the height of outlet vent in the direction of air flow and D is the honeycomb diameter. In some embodiments, the outlet vent 24 includes louvers, slots, or other appropriate geometry such that the features and advantages described herein are achieved.

Another feature that can inhibit or prevent contaminants or other matter from entering the goggle 10 is the vent shield 32. As illustrated in FIGS. 7 and 8, in some embodiments, the vent shield 32 surrounds the outlet vent 24 and directs snow and other solids away from the vent outlet 24. Certain embodiments of the vent shield 32 attach to or are integral with the top surface 26 of the goggle frame 16. In the illustrated embodiment, the vent shield 32 extends upward and rearward to a sufficient height that the air flow through the outlet vent 24 is substantially shielded and/or unaffected. In certain embodiments, the vent shield 32 extends rearward at least as far as the outlet vent 24 so that any snow or other solid matter falling vertically toward the vent 24 will be deflected by the vent shield 32. However, the vent shield 32 may be smaller if desired (e.g., to reduce drag by the goggle 10 overall). As shown in FIG. 7, the vent shield 32 may additionally include sides 44. The vent shield 32 may comprise a variety of shapes designed for various functional or stylistic purposes.

Figure 3C:
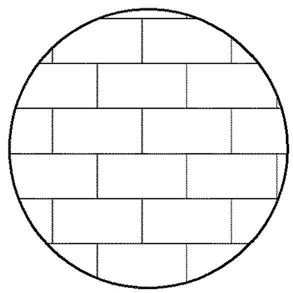
Figure 3D:
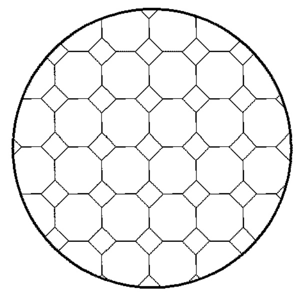
Figure 3E:
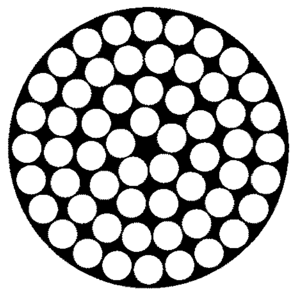
Figure 3F:
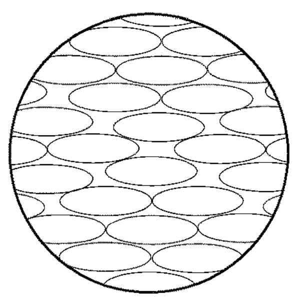
FIG. 3*f* illustrates a repeating elliptical vent shape useful in another embodiment of a goggle in accordance with certain features and advantages disclosed herein.

As mentioned above, the inlet and outlet vents 20, 24 may comprise honeycomb shapes when viewed in cross section. As shown in FIGS. 2 and 3, such a honeycomb shape may comprise a plurality of tessellated regular hexagons. Those skilled in the art will recognize that many other shapes may also be employed. For example, FIGS. 3*a*-3*e* show exemplary alternative shapes such as triangles (FIG. 3*a*), rectangles (FIG. 3*b*), square and/or octagonal honeycombs (FIG. 3*c*), circles (FIG. 3*d*), and ellipses (FIG. 3*e*). FIG. 3*c* also demonstrates that a combination of shapes may be employed, such as to optimize air flow and/or heat transfer in specific locations along the top and/or bottom of the goggle 10. In certain arrangements, the vents 20, 24 are extrusions of the desired shape. However, the vents 20, 24 may be formed by a variety of other processes, such as injection molding, machining, casting, etc.

As illustrated in FIGS. 8, 8*a*, and 8*b*, the walls 46 of the antifogging element 18 can define a plurality of similar flow paths 48. The flow paths 48 may comprise a substantially vertical and straight flow path 48 (see FIG. 8), a substantially non-vertical and straight flow path (see FIG. 8*a*), a tortuous pathway (such as a curved, sinusoidal, undulating, or zigzagged path (see FIG. 8*b*)), or any other flow path which will provide adequate surface area and sufficient air flow as described herein. A flow path that is substantially straight and oriented substantially vertically, will typically provide a low degree of air flow resistance due to a low degree of contact between the air and the walls 46. As the angle of the vent walls relative to a vertical plane increases, the contact between the air and the vent walls can also increase. Providing the zigzagged shape can further increase the air-wall contact. Further, as contact between the air and vent walls 46 increases, the resistance to air flow (drag) and the rate of heat transfer between the vent walls 46 and the air will also increase.

In some embodiments, the vent shield 32 is configured to permit access to the cartridge 90. For example, in the embodiment illustrated in FIGS. 8 and 9, the vent shield 32 is configured to move between a first position (FIG. 8), in which the vent shield is positioned so as to shelter the cartridge 90, and a second position (FIG. 9), in which the vent shield 32 is positioned so as to allow the cartridge 90 to be inserted and/or removed from the vent 20. Such a configuration can, for example, provide protection to the cartridge 90 while also facilitating installation and replacement of the cartridge 90. As shown, in some embodiments, the vent shield 32 pivots between the first and second positions. In other implementations, the vent shield 32 slides between the first and second positions. In yet other instances, the vent shield is connected with the frame 16 in the first position and detached from the frame 16 in the second position.

With reference to FIG. 8, an example of the passive anti-fogging venting system will now be described in which convection has been optimized. With the goggle 10 in the worn position, heat exchangers 28 will typically reach an equilibrium temperature which is warmer than the ambient air outside the goggle space 11 due to the thermal communication with the wearer's face. This temperature difference will cause air at the bottom 53 of the inlet vents 20 to heat up, and rise upward through the flow path of the inlet vents 20. This upward-flowing air will be heated by the walls 46 of the heat exchangers 28 until it passes the heat exchanger top edge 40, and enters the goggle space 11. The air entering the goggle space 11 from the inlet vents 20 may be at a slightly higher temperature than the air previously within the goggle space 11. This warmer air will continue to flow upward within the goggle space 11 as indicated by arrows 54, and finally exiting the goggle space 11 through the outlet vent 24, which is substantially non-conductive of heat and is positioned near or at the top of the goggle 26. Accordingly, the air flow through the goggle space 11 can be driven by the heating of the air passing through the heat exchangers 28. This flow of air is shown in FIGS. 8 and 10 by arrows 54.

Antifogging elements 18 as described elsewhere herein may be positioned at any location which is in airflow communication with the space 11 between the wearer's face and the lens 12. The heat exchanger 28 may also be the antifogging element 18. Alternatively, or in addition, the antifogging element 24 may be positioned in an outlet vent at the top of the goggle.

In various embodiments, the goggle 10 includes one or more electronic components, such as a blower (e.g., a fan), heater, and/or sensor. For example, the goggle 10 can include a temperature sensor, relative or absolute humidity sensor, altitude sensor, location sensor (e.g., GPS sensor), or otherwise. In various embodiments, the temperature and/or humidity sensor is configured to detect the temperature and/or humidity within the space between the user's face and the goggle 10, of the ambient environment (e.g., outside the goggle 10) or otherwise.

In some implementations, the goggle 10 can include a controller, such as a processor and a memory. The controller can receive electrical power from a power source, such as a battery, solar panel, or otherwise. The controller can be configured to control operation of the one or more electronic components. For example, the controller can receive input data related to the temperature and/or humidity in the space between the user's face and the goggle 10 from a temperature and/or humidity sensor. In various implementations, the controller can initiate an action in response to the input data. For example, the controller can activate the fan when the humidity is greater than or equal to a set-point value (e.g., a relative humidity of at least about: 70%, 80%, 90%, 95%, 99%, 100%, values between the aforementioned values, or otherwise). In certain implementations, the set-point value is constant. In some variants, the set-point value is dynamic. For example, the set-point value can change as a function of the ambient temperature and/or humidity (e.g., the set-point value can decrease as the ambient temperature decreases).

In some embodiments, the goggle 10 includes an electrochromic functional layer, which can include a dichroic dye guest-host device configured to provide variable light attenuation. For example, a functional layer can include spaced substrates coated with a conducting layer, an alignment layer, and preferably a passivation layer. Disposed between the substrates is a guest-host solution which includes a host material and a light-absorbing dichroic dye guest. Additional details regarding electrochromic functional layers can be found in U.S. Publication No. 2013/0141693, the entire contents of which are incorporated herein by reference.

A power circuit can be supplied to the functional layer through a battery in the host eyewear. The power circuit provides a supply of electrical power to the conducting layers. Adjustment of the power supply alters the orientation of the host material which in turn alters the orientation of the dichroic dye. Light is absorbed by the dichroic dye, depending upon its orientation, and thus provides variable light attenuation, that can be manually adjusted by the wearer. Such a dichroic dye guest-host device is disclosed in U.S. Pat. No. 6,239,778, the entire contents of which are incorporated herein by reference.

In some embodiments, an electrochromic functional layer is produced by depositing a composition containing a cross-linkable polymer onto a suitable support followed by in situ crosslinking. For example, a polymerizable composition can be applied onto a glass plate coated with a layer of WO.sub.3 and a tin oxide conductive sublayer, and photopolymerized by UV irradiation to obtain a membrane that is optically transparent in the visible range and adherent to the support. The membrane can then be assembled with a counterelectrode formed on a glass plate bearing a layer of hydrogenated iridium oxide H.sub.xIrO.sub.2 and a tin oxide sublayer. The polymerizable composition can be formed from the lithium salt of trifluoro-methanesulfonyl(1-acryloyl-2,2,2-tri-fluoroethanesulfonyl)imide-, poly(theylene glycol) dimethacrylate, silica particles, and xanthone. In some embodiments, an electrochromic layer is formed by two electrochromic layers separated by a film of ion-conducting material. Each electrochromic layer can be borne by a substrate coated with a conductive oxide, an indium tin oxide-based material, a zinc oxide-based material, or another type of conductive layer. The ion-conducting material forms an ion-conducting polymer electrolyte and is formed by a proton-conducting polymer, for example a 2-acrylamido-2-methylpropanesulfonic acid homopolymer. The polymer film can be produced by depositing onto one of the electrodes a liquid reaction mixture containing the polymer precursor dissolved in a liquid solvent, for example a mixture of water and NMP.

In some embodiments, an electrochromic layer includes an electrode and a counterelectrode separated by a solid polymer electrolyte. The electrode can be formed by a transparent substrate bearing an electronically conductive film coated with a film of a cathode active material with electrochromic properties. The counterelectrode can be formed by a transparent substrate bearing an electronically conductive film coated with a film of an anode active material with electrochromic properties. The electrolyte can be formed by an ion-conducting material including a salt dissolved in a solvating solid polymer. In some implementations, the electrolyte membrane is intercalated in the form of a composition of low viscosity free of volatile liquid solvent and/or includes a polymer or a polymer precursor and a salt.

In some embodiments, the goggle 10 can include a module, which can comprise visual display and/or optical components. These components can include a display such as a liquid crystal display (LCD), plasma display, a semiconductor device (LD), light-emitting diode (LED), organic light emitting diode (OLED), active OLED, AMOLED, super AMOLED, projector, direct retinal projection through virtual retinal display (VRD) or retinal scan display (RSD) using a retinal projector (RP), micro-electro-mechanical systems display, electroluminescence (EL), cathode ray tube (CRT), digital micromirror device (DMD), prism(s), lens (es), fiber-optic transmission component(s), mirror(s), holographic optical element (HOE), laser projection, 3D display components or circuitry, or another emissive, transmissive, or reflective display technology, or the like. The system can produce real or virtual images for user perception. Certain embodiments of the system can provide augmented visuals of natural objects perceived by the user.

The viewing plane for the system can be on a lens of the goggle 10 or spaced from the lens (either in front or behind the lens). The viewing plane can be real or virtual. The system and/or eyewear can comprise variable light attenuation features (e.g. electronic variable light attenuation) in the lens(es) or otherwise to enhance video display perception. The viewing plane can incorporate one or more display and/or light attenuation components.

Several embodiments of the goggle 10 include video input and/or output devices, components, circuitry, methods, and/or other structures. For example, the goggle 10 can include one or more of the features disclosed in any of the following U.S. Patent and Publication Nos.: U.S. Publication No. 2005/0219152 (disclosing a microdisplay with virtual image and an adjustable boom), U.S. Publication No. 2009/0015929 (disclosing a substrate guided relay), U.S. Publication No. 2010/0111472 (disclosing a substrate guided relay), U.S. Publication No. 2010/0053591 (disclosing image projection technology), U.S. Publication No. 2009/0180195 (disclosing heads-up display and imaging systems), U.S. Publication No. 2011/0043644 (disclosing devices and methods for providing localized image enhancements in a heads-up display), U.S. Publication No. 2012/0105740 (disclosing detachable adjustable electronics modules connected to eyewear), U.S. Pat. No. 7,740,353 (disclosing a direct retinal projection heads-up display), U.S. Pat. No. 7,639,209 (disclosing structures and methods related to retinal projection), U.S. Pat. No. 7,631,968 (disclosing devices for heads-up displays), U.S. Pat. No. 7,249,846 (disclosing a heads-up display device), U.S. Pat. No. 7,192,137 (disclosing heads-up display devices), U.S. Pat. No. 7,158,096 (disclosing heads-up display and transmission devices), U.S. Pat. No. 7,023,621 (disclosing images superimposed on field of view), U.S. Pat. No. 5,369,415

(disclosing direct retinal projection), U.S. Pat. No. 5,596,339 (disclosing retinal display using a fiber optic point source), the entireties of each of which are incorporated herein by reference.

Following is an illustrative listing of certain additional embodiments within the scope of this disclosure. These embodiments are examples only and are not intended to be limiting. Although there may be some embodiments within the scope of this disclosure that are not expressly recited below or elsewhere herein, the present disclosure contemplates and includes all embodiments within the scope of what this disclosure shows and describes. Further, this disclosure contemplates and includes embodiments comprising any combination of any structure, material, step, or other feature disclosed anywhere herein with any other structure, material, step, or other feature disclosed anywhere herein.

Embodiment 1

A goggle comprising: a goggle frame configured to be worn on a wearer's face; a lens coupled with the frame; a flow path having an influent port and an effluent port, the path being defined at least by the frame, the lens, and the wearer's face; and a regenerable antifogging element in communication with the flow path, the antifogging element including a hydrophilic material configured to absorb moisture under a first set of conditions while on a wearer's face, and release moisture under a second set of conditions while on the wearer's face.

Embodiment 2

The goggle of Embodiment 1, further comprising a cartridge configured to be removably received by the goggle, the cartridge including the antifogging element.

Embodiment 3

The goggle of Embodiment 1 or Embodiment 2, wherein the cartridge is located at the effluent port.

Embodiment 4

The goggle of any of Embodiments 1-3, wherein the hydrophilic material comprises acetate.

Embodiment 5

The goggle of any of Embodiments 1-4, wherein the hydrophilic material comprises cellulose acetate proprionate.

Embodiment 6

The goggle of any of Embodiments 1-5, wherein the effluent port is located at an upper surface of the frame.

Embodiment 7

The goggle of any of Embodiments 1-6, wherein an interior surface of the goggle comprises the hydrophilic material.

Embodiment 8

The goggle of any of Embodiments 1-7, wherein the hydrophilic material is carried by an interior surface of the goggle.

Embodiment 9

The goggle of any of Embodiments 1-8, wherein the goggle frame comprises the regenerable antifogging element.

Embodiment 10

The goggle of any of Embodiments 1-9, further comprising a blower configured to provide a flow of air along the flow path.

Embodiment 11

The goggle of any of Embodiments 1-10, further comprising a heating element disposed on the goggle and configured to provide heat to the goggle.

Embodiment 12

The goggle of any of Embodiments 1-11, further comprising a sensor.

Embodiment 13

The goggle of Embodiment 12, wherein the sensor comprises a humidity sensor configured to detect the humidity in a space between the goggle and the wearer's face.

Embodiment 14

The goggle of any of Embodiments 1-13, wherein an airflow along the flow path is greater during the second set of conditions than during the first set of conditions.

Embodiment 15

A passive anti-fogging goggle comprising: a goggle frame having an upper surface, a lower surface, and left and right sides; a lens held by the frame, defining an enclosed volume between the lens and a wearer's face; an inlet vent located on a lower portion of the goggle, the inlet vent configured to allow air flow therethrough; an outlet vent on the goggle; and an antifogging element having a cellulose acetate proprionate surface exposed to the volume, the cellulose acetate proprionate surface having been exposed to sodium hydroxide to create a reversible water absorbing characteristic.

Embodiment 16

The goggle of Embodiment 15, further comprising a cartridge configured to be received in and removable from the goggle, the cartridge including the antifogging element.

Embodiment 17

The goggle of Embodiment 15 or Embodiment 16, wherein the antifogging element comprises a substantially honeycomb shape.

Embodiment 18

The goggle of any of Embodiments 15-17, wherein the cellulose acetate proprionate surface is on a portion of the goggle frame.

Embodiment 19

The goggle of any of Embodiments 15-18, wherein the cellulose acetate proprionate surface is permanently attached to the goggle.

Embodiment 20

A ski goggle kit comprising: a substantially enclosed goggle space having a volume and defined at least by a lens, a frame, and a face of a wearer; an inlet vent and an outlet vent, the vents in communication with the goggle space and disposed and configured to produce a uni-directional, buoyancy-driven air flow through the goggle space; and a first moisture-absorbing cartridge and a second moisture-absorbing cartridge, the first and second cartridges configured to be received in at least one of the inlet vent and the outlet vent one at a time, the first and second cartridges having different levels of moisture absorbency, thereby producing different levels of drying on the air flow; wherein the goggle kit is configured to allow the wearer to select, based on the desired level of moisture absorbency, which of the cartridges is received in the inlet vent.

Embodiment 21

The goggle kit of Embodiment 20, further comprising at least one heat conductive element configured to conduct heat from the wearer's face to the inlet vent.

Embodiment 22

The goggle kit of Embodiment 21, wherein the inlet vent comprises a plurality of air passageways extending through a substantially honeycomb shape.

Embodiment 23

A method of manufacturing a fogging-resistant ski goggle, the method comprising: providing a frame with an inlet vent at a bottom of the frame and an outlet vent at a top of the frame, the frame being configured to produce a unidirectional free convectional flow of air from the inlet vent through the outlet vent; providing a cellulose acetate proprionate hydrophilic element configured to reduce the humidity of the flow of air; and mounting the hydrophilic element in communication with the flow of air.

Embodiment 24

The method of Embodiment 22, further comprising providing a vent shield at a top surface of the goggle.

Embodiment 25

A method of producing a moisture-reduced unidirectional flow of air in a ski goggle, the method comprising: positioning the goggle on a wearer's face, the goggle including a substantially heat conductive inlet vent on a lower surface of the goggle and an outlet vent on a top surface of the goggle; heating the inlet vent, thereby producing a unidirectional flow of air from the inlet vent to the outlet vent, wherein the inlet vent and the outlet vent are in communication with a space between a lens of the goggle and the wearer's face; and inserting a moisture absorbent element in at least one of the inlet vent and the outlet vent.

Embodiment 26

The method of Embodiment 25, wherein inserting the moisture absorbent element is accomplished by inserting a cartridge comprising a hydrophilic material in the vent.

Embodiment 27

A method of customizing a fog-resistant goggle, the method comprising: estimating the moisture content of the ambient environment; selecting a moisture absorbing cartridge with sufficient moisture absorptivity to inhibit the moisture content of the ambient environment from condensing on the goggle when the goggle is worn by a user in the ambient environment; and inserting the moisture absorbing cartridge into the goggle.

Embodiment 28

An antifogging element for releasable connection to a goggle, comprising: a frame; a plurality of sidewalls carried by the frame, the sidewalls defining a plurality of flow paths from an inlet side of the frame to an outlet side of the frame; a hydrophilic surface on at least 50% of the exposed surface area of the sidewalls; wherein the hydrophilic surface, once saturated with water, can lose at least 50% of its retained water in less than 20 minutes at a temperature of less than about 100 degrees F.

Embodiment 29

The antifogging element of Embodiment 28, further comprising at least one connector, for locking the frame to a complementary connector on a goggle.

Embodiment 30

The antifogging element of Embodiment 28 or Embodiment 29, wherein the surface comprises activated cellulose acetate proprionate.

Although certain embodiments and examples of goggles and methods have been described herein, it will be understood by those skilled in the art that the present inventive subject matter extends beyond the specifically disclosed embodiments to other alternative embodiments and/or uses of the goggles and obvious modifications and equivalents thereof. Various features and aspects of the disclosed embodiments can be combined with or substituted for one another in order to form varying modes of the goggles. For example, the anti-fogging element (e.g., an activated acetate element) can be used in combination with any other feature within the scope of this disclosure, such as in combination with an airflow path, fan, heater, and/or sensor.

Certain features that are described in this disclosure in the context of separate implementations can also be implemented in combination in a single implementation. Conversely, various features that are described in the context of a single implementation can also be implemented in multiple implementations separately or in any suitable subcombination. Also, although features may be described above as acting in certain combinations, one or more features from a claimed combination can, in some cases, be excised from the combination, and the combination may be claimed as any subcombination or variation of any subcombination.

While operations may be depicted in the drawings or described in the specification in a particular order, such operations need not be performed in the particular order shown or in sequential order, and that all operations need not be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein (e.g., the terms "approximately," "about," "generally," and "substantially") is intended to have its ordinary meaning, such as representing a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise. As yet another example, in certain embodiments, the terms "generally perpendicular" and "substantially perpendicular" refer to a value, amount, or characteristic that departs from exactly perpendicular by less than or equal to 15 degrees, 10 degrees, 5 degrees, 3 degrees, 1 degree, 0.1 degree, or otherwise.

Some embodiments have been described in connection with the accompanying drawings. The figures are drawn to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Any methods described herein may be practiced using any device suitable for performing the recited steps.

In summary, various embodiments and examples of regeneratable anti-fogging goggles and methods have been disclosed. Although the regeneratable anti-fogging goggles and methods have been disclosed in the context of those embodiments and examples, it will be understood by those skilled in the art that this disclosure extends beyond the specifically disclosed embodiments to other alternative embodiments and/or other uses of the embodiments, as well as to certain modifications and equivalents thereof. For example, some embodiments can be configured to be used with other types of goggles or configurations, such as goggles for riding a vehicle (e.g., a bicycle or motorcycle), goggles for non-alpine sports (e.g., for racquetball or basketball), or otherwise. This disclosure expressly contemplates that the various features and aspects of any embodiments within the scope of this disclosure can be combined with, or substituted for, one another. Thus, it is intended that the scope of the present inventive subject matter herein disclosed should not be limited by the particular disclosed embodiments described above, but should be determined only by a fair reading of the appended claims.

What is claimed is:

1. A goggle comprising:

a goggle frame configured to be worn on a wearer's face;

a lens coupled with the goggle frame;

a flow path having an influent port and an effluent port, the flow path being defined at least by the goggle frame and the lens; and a cartridge configured to be removably received in the goggle frame, the cartridge comprising a regenerable antifogging element in communication with the flow path, the regenerable antifogging element including a hydrophilic material configured to absorb moisture under a first set of conditions while on the wearer's face, and to release the absorbed moisture under a second set of conditions while on the wearer's face, the regenerable antifogging element thereby configured to regenerate a water absorption characteristic of the hydrophilic material under the second set of conditions, the second set of conditions occurring when the wearer is moving relative to a surrounding environment, and ambient air circulates into the flow path of the goggle, wherein the hydrophilic material comprises an activated acetate that has been exposed to sodium hydroxide to make the water absorption characteristic of the antifogging element regenerable.

2. The goggle of claim 1, wherein the cartridge is located at the effluent port.

3. The goggle of claim 1, wherein the hydrophilic material comprises cellulose acetate propionate.

4. The goggle of claim 1, wherein the effluent port is located at an upper surface of the ski goggle frame.

5. The goggle of claim 1, wherein the hydrophilic material is carried by an interior surface of the goggle when the cartridge is received in the goggle frame.

6. The goggle of claim 1, wherein the activated acetate comprises cellulose acetate propionate, polycellulose acetate, cellulose acetate, cellulose acetobutyrate, or cellulose acetopropionate.

7. A ski goggle kit comprising:

a substantially enclosed goggle space having a volume and defined at least by a lens and a frame;

an inlet vent and an outlet vent, each vent in communication with the goggle space and disposed and configured to produce a uni-directional, buoyancy-driven air flow through the goggle space; and a first moisture-absorbing cartridge and a second moisture-absorbing cartridge, the first and second cartridges configured to be received in at least one of the inlet vent and the outlet vent, the first and second cartridges having different levels of moisture absorbency, thereby producing different levels of drying on the air flow;

wherein the ski goggle kit is configured to allow a wearer to select, based on a desired level of moisture absorbency, which of the cartridges is received in the inlet vent;

wherein at least one of the first moisture-absorbing cartridge or the second moisture-absorbing cartridge comprises a hydrophilic material, and is configured to regenerate a water absorption characteristic of the hydrophilic material when the wearer is moving relative to a surrounding environment, causing the uni-directional, buoyancy-driven air flow through the goggle space, wherein the hydrophilic material comprises an activated acetate that has been exposed to sodium hydroxide to make the water absorption characteristic of the hydrophilic material regenerable.

8. The ski goggle kit of claim 7, further comprising at least one heat conductive element configured to conduct heat from the wearer's face to the inlet vent.

9. The ski goggle kit claim 8, wherein the inlet vent comprises a plurality of air passageways extending through a substantially honeycomb shape.

10. The ski goggle kit of claim 7, wherein the activated acetate comprises cellulose acetate propionate, polycellulose acetate, cellulose acetate, cellulose acetobutyrate, or cellulose acetopropionate.

11. A method of manufacturing a fogging-resistant ski goggle, the method comprising:

providing a frame with an inlet vent at a bottom of the frame and an outlet vent at a top of the frame, the frame being configured to produce a unidirectional free convectional flow of air from the inlet vent through the outlet vent;

providing a cartridge comprising a cellulose acetate propionate hydrophilic material configured to reduce the humidity of the flow of air; and mounting the cartridge in the frame such that the cellulose acetate propionate hydrophilic material is in communication with the flow of air;

wherein the cellulose acetate propionate hydrophilic material is configured to absorb moisture under a first set of conditions while on a wearer's face, and to release the absorbed moisture under a second set of conditions while on the wearer's face, the cellulose acetate propionate hydrophilic material thereby configured to regenerate a water absorption characteristic under the second set of conditions, the second set of conditions occurring when the wearer is moving relative to a surrounding environment, and the flow of air is produced in the goggle, wherein the cellulose acetate propionate hydrophilic material has been exposed to sodium hydroxide to make the water absorption characteristic of the cellulose acetate propionate hydrophilic material regenerable.

12. The method of claim 11, further comprising providing a vent shield at a top surface of the ski goggle.

* * * * *